(12) United States Patent
Chudy et al.

(10) Patent No.: US 8,571,886 B2
(45) Date of Patent: Oct. 29, 2013

(54) SYSTEM AND METHOD FOR MANAGEMENT OF PHARMACY WORKFLOW

(75) Inventors: Duane S. Chudy, Lincolnshire, IL (US); David A. Schultz, Palatine, IL (US)

(73) Assignee: AutoMed Technologies, Inc., Buffalo Grove, IL (US)

( * ) Notice: Subject to any disclaimer, the term of this patent is extended or adjusted under 35 U.S.C. 154(b) by 0 days.

(21) Appl. No.: 12/953,140

(22) Filed: Nov. 23, 2010

(65) Prior Publication Data

US 2011/0131056 A1    Jun. 2, 2011

Related U.S. Application Data

(62) Division of application No. 10/283,529, filed on Oct. 30, 2002, now Pat. No. 7,860,724.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......... 705/2–4; 700/237, 241, 230, 233, 216, 700/228; 221/2, 6, 7
See application file for complete search history.

(56) References Cited

U.S. PATENT DOCUMENTS

| | | | |
|---|---|---|---|
| 4,847,764 A | 7/1989 | Halverson | |
| 4,971,513 A | 11/1990 | Bergerioux et al. | |
| 5,208,762 A | 5/1993 | Charhut et al. | |
| 5,259,499 A | 11/1993 | Boettger | |
| 5,317,506 A | 5/1994 | Coutre et al. | |
| 5,323,908 A | 6/1994 | Boettger | |
| 5,597,995 A * | 1/1997 | Williams et al. | 235/375 |
| 5,666,492 A | 9/1997 | Rhodes et al. | |
| 5,713,485 A * | 2/1998 | Liff et al. | 221/2 |
| 5,713,487 A | 2/1998 | Coughlin | |
| 5,737,539 A | 4/1998 | Edelson et al. | |
| 5,758,095 A | 5/1998 | Albaum et al. | |
| 5,761,877 A | 6/1998 | Quandt | |
| 5,762,235 A | 6/1998 | Coughlin | |
| 5,797,515 A | 8/1998 | Liff et al. | |
| 5,845,255 A | 12/1998 | Mayaud | |

(Continued)

FOREIGN PATENT DOCUMENTS

| | | | |
|---|---|---|---|
| CA | 2 307 153 A1 | 10/2000 | |
| CA | 2 413 065 A1 | 12/2001 | |
| GB | 2 003 831 | 3/1979 | |

OTHER PUBLICATIONS

Baxter Healthcare Corporation, Operator's Manual, 1994.

(Continued)

*Primary Examiner* — Michelle Le
(74) *Attorney, Agent, or Firm* — Reinhart Boerner Van Deuren s.c.

(57) ABSTRACT

A system and method for optimized management of pharmacy workflow, specifically, workflow associated with fulfillment of prescription orders for medications and health-related products in a pharmacy environment. A computer-controlled system coordinates and controls pharmacy workflow to sequence prescriptions for fulfillment in a most efficient path thereby minimizing a cost function associated with fulfillment of the prescription order. The system coordinates and controls prescription order fulfillment from automated and non-automated storage locations and can be easily adapted to the specific layout and level of automation desired by the operator.

18 Claims, 25 Drawing Sheets

(56) References Cited

U.S. PATENT DOCUMENTS

| | | | |
|---|---|---|---|
| 5,883,370 A | 3/1999 | Walker et al. | |
| 5,907,493 A * | 5/1999 | Boyer et al. | 700/231 |
| 5,988,858 A | 11/1999 | Yuyama et al. | |
| 6,021,392 A | 2/2000 | Lester et al. | |
| 6,068,156 A | 5/2000 | Liff et al. | |
| 6,112,182 A | 8/2000 | Akers et al. | |
| 6,152,364 A | 11/2000 | Schoonen et al. | |
| 6,155,485 A | 12/2000 | Coughlin et al. | |
| 6,170,230 B1 | 1/2001 | Chudy et al. | |
| 6,181,979 B1 | 1/2001 | Murakami | |
| 6,202,923 B1 | 3/2001 | Boyer et al. | |
| 6,219,587 B1 | 4/2001 | Ahlin et al. | |
| 6,256,967 B1 | 7/2001 | Hebron et al. | |
| 6,283,322 B1 | 9/2001 | Liff et al. | |
| 6,308,109 B1 | 10/2001 | Yuyama et al. | |
| 6,317,648 B1 | 11/2001 | Sleep et al. | |
| 6,318,630 B1 | 11/2001 | Coughlin et al. | |
| 6,330,351 B1 | 12/2001 | Yasunaga | |
| 6,330,491 B1 | 12/2001 | Lion | |
| 6,351,688 B1 | 2/2002 | Nichols et al. | |
| 6,352,200 B1 | 3/2002 | Schoonen et al. | |
| 6,421,584 B1 | 7/2002 | Norberg et al. | |
| 6,438,451 B1 | 8/2002 | Lion | |
| RE37,829 E | 9/2002 | Charhut et al. | |
| 6,449,927 B2 | 9/2002 | Hebron et al. | |
| 6,529,801 B1 | 3/2003 | Rosenblum | |
| 2001/0002448 A1 | 5/2001 | Wilson et al. | |
| 2001/0025208 A1 | 9/2001 | Bartur | |
| 2002/0032582 A1 | 3/2002 | Feeney, Jr. et al. | |
| 2002/0062175 A1 | 5/2002 | Lion | |
| 2003/0149599 A1 * | 8/2003 | Goodall et al. | 705/2 |
| 2003/0225595 A1 | 12/2003 | Helmus et al. | |
| 2004/0088187 A1 | 5/2004 | Chudy et al. | |

OTHER PUBLICATIONS

Baxter Healthcare Corporation, Operator's Manual, 1995.
Baxter Healthcare Corporation, System Proposal, Apr. 21, 1998.
Canadian Office Action for Application No. 2,410,397, dated Jan. 13, 2009, 6 pages.
ElectroCom Automation L.P., Functional Specification, Jun. 13, 1994.
Excerpt from U.S. Pharmacist Magazine, 2001, 2 pages.
Notice of Allowance for U.S. Appl. No. 10/283,529, mail date Aug. 23, 2010, 7 pages.
Office Action for U.S. Appl. No. 10/283,529, mail date Apr. 15, 2009, 8 pages.
Office Action for U.S. Appl. No. 10/283,529, mail date Dec. 31, 2007, 13 pages.
Office Action for U.S. Appl. No. 10/283,529, mail date Jul. 3, 2007, 12 pages.
Office Action for U.S. Appl. No. 10/283,529, mail date Jun. 27, 2008, 13 pages.
Office Action for U.S. Appl. No. 10/283,529, mail date Nov. 3, 2009, 18 pages.

* cited by examiner

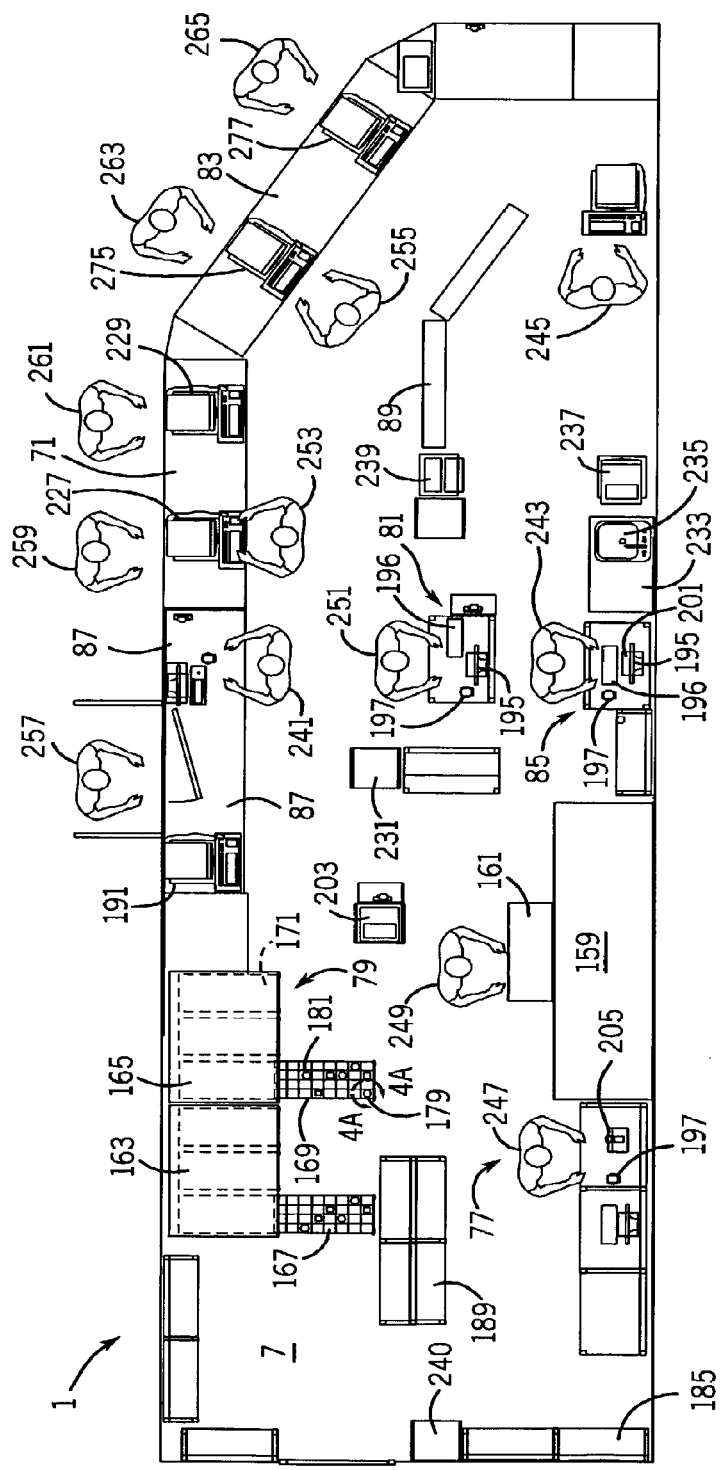
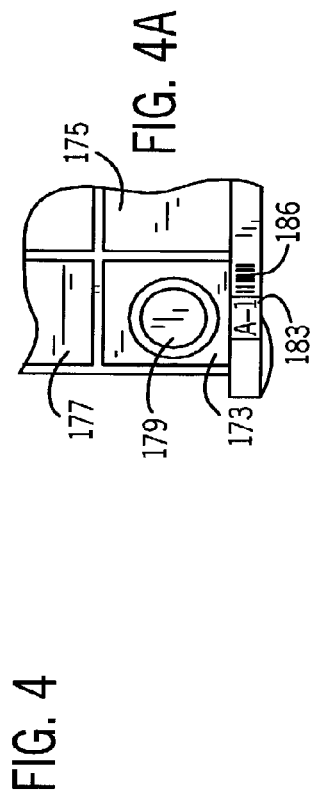
FIG. 4
FIG. 4A

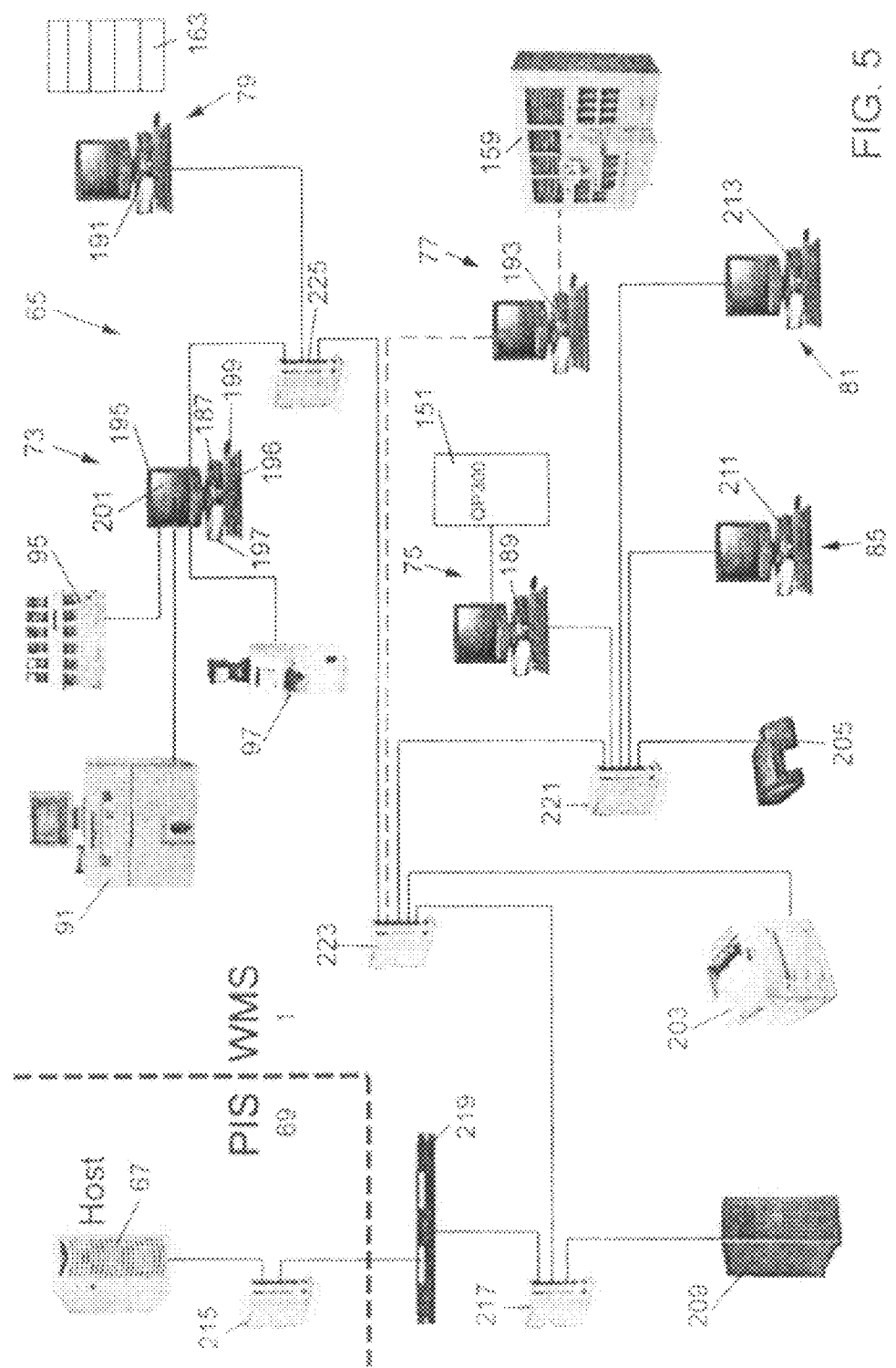

SYSTEM AND METHOD FOR MANAGEMENT OF PHARMACY WORKFLOW

CROSS-REFERENCE TO RELATED PATENT APPLICATIONS

This is a divisional application of application Ser. No. 10/283,529, filed Oct. 30, 2002, which is incorporated herein by reference in its entirety.

FIELD OF THE INVENTION

The present invention relates to management of work flow in a pharmacy environment. More particularly, the invention relates to a system and method for optimized fulfillment of prescription orders within the pharmacy.

BACKGROUND OF THE INVENTION

Pharmacies are an important source of medications and health-related products for a wide range of people including, for example, retail customers, hospitalized patients and residents of alternate site (e.g., long term care) facilities. The pharmacy which serves the needs of such people may be located for instance, in a retail environment, such as a drugstore, or a facility adjunct to the hospital or alternate site facility. A typical pharmacy is staffed by at least one registered pharmacist and is further staffed by trained pharmacy technicians and clerks.

Pharmacy personnel provide a broad range of services and information. For example, the pharmacist typically has overall responsibility for ensuring that all prescription orders for medications and health-related products are fulfilled properly. The pharmacy technicians may assist the pharmacist in fulfillment of the prescription orders and in replenishment of the medication inventory. Pharmacists and pharmacy technicians commonly provide other important service such as interaction with customers, doctors and care givers, the provision of health-related advice, data entry and processing of medical and financial information adjunct to fulfillment of the prescription orders. Provision of advice and information may include direct interaction with others while data processing and order fulfillment typically involve interaction between the pharmacy personnel and a computer or with the medications and products needed to fulfill the prescription orders. For example, fulfillment of the prescription orders may involve locating one or more medications or products at a static storage shelf or other storage location, dispensing a quantity of the medications or products required to fill each prescription comprising the order, manually packaging the medications in containers (such as bottles and vials) and dispensing the packaged medications and products to the customer, doctor or care giver.

It is highly desirable for the pharmacist and pharmacy technician personnel to be available to provide high value added services, such as providing health-related advice and information to customers, doctors and care givers. It is also desirable to fulfill each prescription order in terms of the lowest possible cost function. Such cost function may be defined in terms of many variables, such as the total time required to fulfill each prescription order, the spacial distance traveled by the pharmacy personnel within the pharmacy in order to fulfill each prescription order and the cost to the pharmacy of the medication and products used to fulfill each prescription order. The cost function may also be defined in terms of cost reduction through coordination of the fulfillment of co-pending prescription orders. A further critical requirement of the pharmacy is the need for accuracy and error avoidance in the fulfillment of the prescription orders.

To these and other ends, there has been a growing use and acceptance of automation in connection with fulfillment of prescription orders by pharmacies. Such automation can include the use of computerized information databases for processing medical and financial information, the use of automated apparatus for dispensing medications and articles and the use of machine-readable code (e.g., bar coding) for purposes of ensuring accuracy in fulfillment of the prescription orders and in maintaining inventory. Any improvement in pharmacy efficiency may result in an overall better level of service to the customer, doctor or care giver.

A major problem confronting the use of automation in the pharmacy environment is the legitimate need for human beings to participate in the prescription order fulfillment process. Pharmacy personnel are required to make many complex decisions and to undertake many tasks to fulfill the prescription orders in an efficient manner. Judgments must be made, for example, as to the medications and products best suited to the customer's needs and the most efficient path by which to locate, obtain, package and dispense the contents of each prescription order, and to do this in a manner which minimizes the potential for error. Moreover, human beings require time to fulfill the prescription orders including the time required to move spatially within the pharmacy from storage location to storage location. In fact, it has been demonstrated that a pharmacy employee may walk as much as five miles throughout the pharmacy during the course of a typical work week; this represents a time component which contributes to the cost function associated with fulfillment of the prescription orders. Consequently, the use of pharmacy automation must coordinate human and machine resources to fulfill each prescription order at the lowest cost function with the highest possible level of error avoidance.

While there are a number of pharmacy automation systems and products described in the art, those systems and products do not disclose systems for optimized management of workflow associated with fulfillment of the prescription orders. For example, U.S. Pat. No. 5,597,995 (Williams et al.) describes a prescription fulfillment system which requires imaging, filling and checking work stations. Medication is dispensed into containers at the filling work station from a collection of automated dispenser apparatus or from static storage locations. While certain efficiencies are derived from use of automated dispenser apparatus, the '995 patent fails to describe any coordinated and optimized use of the system components to select medications with the lowest cost function and fail to disclose any procedure or apparatus to efficiently sequence the prescriptions comprising fulfillment of the prescription orders thereby optimally reducing the cost function associated with the fulfillment process.

U.S. Pat. No. 5,907,493 (Boyer et al.) describes a pharmaceutical dispensing system for filling prescriptions in a pharmacy setting. A central computer controls a plurality of pill dispensing cells each of which are stated to include helical singulation apparatus each under the control of a separate microprocessor. Medications may also be stored for dispensing at shelf locations. While the central computer is stated to store information regarding a plurality of drugs in predetermined, separately-addressable cells and to arrange that information to provide optimum efficiency of pharmaceutical operations, such assertion of efficiency does not include any coordinated and optimized use of the system components to select optimized medications for each prescription and then sequence filling of the prescription so as to optimally reduce the cost function associated with the prescription order fulfillment process.

An automated pharmacy is described in U.S. Pat. No. 6,202,923 (Boyer et al.). The pharmacy described therein is said to have improved pharmacy throughput because the labels to be affixed to the medication containers are generated once the specified prescription is displayed at a filling workstation thereby avoiding any requirement to manually transfer labels from an upstream data entry workstation. Unfortunately, workflow in the automated pharmacy is not fully optimized because, once again, there is no provision for any optimized sequencing of the prescriptions comprising the prescription order to reduce the cost function associated with the prescription order fulfillment process.

U.S. Pat. No. 6,181,979 (Murakami) discusses a drug preparation system. Data are collected to determine the throughput times of particular drug processing and throughput stations within the system. The information is used to allocate pharmacy personnel to the various drug processing and inspection stations but is not utilized to determine an optimum sequence of prescriptions within an order.

It would be significant improvement in the art to provide an improved pharmacy automation system and method of pharmacy workflow management which would optimally reduce the cost function associated with fulfillment of prescription orders, which would reduce the potential for errors in the fulfillment process, which would be operable to control virtually any type of dispensing and storage apparatus, which would be adaptable for use in many different pharmacy environments, including for example, retail pharmacies, alternate site facilities, hospitals and like facilities, and which would free pharmacists and pharmacy technicians to perform high value added services thereby better serving the customers, doctors and care givers reliant on the pharmacy.

OBJECTS OF THE INVENTION

It is an object of the invention to provide an improved pharmacy automation system and method of pharmacy workflow management overcoming some of the problems and shortcomings of the prior art, including those referred to above.

Another object of the invention is to provide an improved pharmacy automation system and method of pharmacy workflow management which would reduce the cost function associated with fulfillment of prescription orders to an extent not capable of being provided by existing pharmacy automation systems.

An object of the invention is to provide an improved pharmacy automation system and method of pharmacy workflow management which is simple to utilize in the pharmacy environment.

Still another object of the invention is to provide an improved pharmacy automation system and method of pharmacy workflow management which would minimize the need for human involvement in the prescription order fulfillment process.

Yet another object of the invention is to provide an improved pharmacy automation system and method of pharmacy workflow management which would reduce the amount of time required to fulfill a prescription order.

It is also an object of the invention to provide an improved pharmacy automation system and method of pharmacy workflow management which would reduce the spacial distance required to be traveled to fulfill a prescription order.

It is an object of the invention to provide an improved pharmacy automation system and method of pharmacy workflow management which reduces the potential for errors in the fulfillment process.

Another object of the invention is to provide an improved pharmacy automation system and method of pharmacy workflow management which is adaptable for use with a range of pharmacy environments.

A further object of the invention is to provide an improved pharmacy automation system and method of pharmacy workflow management which is adaptable for use with any filling or storage apparatus within the pharmacy.

One additional objective of the invention is to free pharmacy personnel for better service to the pharmacy customers, doctors and care givers.

How these and other objects are accomplished will become apparent from the following descriptions and the drawings.

SUMMARY OF THE INVENTION

In general, the invention is a workflow management system ("WMS") and method for optimized management of pharmacy workflow, specifically, workflow associated with fulfillment of prescription orders for medications and health-related products in a personnel-driven pharmacy operation. (As used herein, the term "medication" is intended to be a broad term including medications as well as health-related products typical of those provided by pharmacies.) Each prescription order fulfilled by the pharmacy includes one or more prescriptions. The medications accessed to fulfill the prescriptions comprising each prescription order may be located at automated and/or non-automated medication storage locations organized into "fulfillment centers" and positioned about the pharmacy.

The WMS coordinates and controls prescription order fulfillment by organizing fulfillment of the prescriptions in the most efficient workflow path and then by directing the pharmacy personnel to and between the fulfillment center automated and/or non-automated medication storage locations to retrieve the required medications, also in the most efficient workflow path. The WMS is intended to make the task of the pharmacy personnel easier and more reliable, thereby providing a higher level of service to the customer. Therefore, the present invention is intended for use in personnel-driven pharmacies where direct human involvement is required to fulfill the prescriptions in the prescription order, and does not relate to fully mechanized and automated facilities, which are outside the scope of the invention.

The invention includes a computer-controlled system of pharmacy management which coordinates fulfillment of each prescription order based on the pharmacy layout and storage location of the medication required to fulfill each prescription within the prescription order. The WMS determines the optimal sequence for fulfillment of each prescription within a prescription order and places the prescriptions within a prescription sequence to minimize the cost function associated with filling the prescription order.

The cost function is established by means of rules which may be developed based on the requirements of the pharmacy operator. Most commonly, those rules will seek to minimize the monetary cost or time required to fill a prescription order. However, other rules may be developed including, for example: (1) rules for reduction of the distance traveled to fulfill a prescription order; (2) rules for reduction of time and distance required to fulfill a prescription order; and (3) rules for reduction of time required to fulfill co-pending prescription orders based on sequenced utilization of the storage locations required for fulfillment of the co-pending prescription orders.

The improvements in efficiency made possible by the invention free valuable pharmacy personnel to perform value added functions such as providing advise and guidance to customers and health care providers. Moreover, the system increases pharmacy throughput and reduces the potential for error further improving pharmacy work flow.

In one embodiment, the WMS for optimized management of workflow associated with fulfillment of medication prescription orders includes a plurality of spaced-apart medication storage locations. Preferably, the storage locations are at fulfillment centers and include automated and/or non-automated dispenser and storage apparatus. However, the precise apparatus selected for the storage locations will be tailored to the needs of the particular pharmacy operator. The system further includes a medication inventory including plural medications stored at predetermined storage locations within the system.

A control computer is provided, preferably as part of a local area network, to receive prescription orders from a host pharmacy information system into a prescription order database. The control computer includes programmed instructions adapted to optimize the pharmacy workflow associated with fulfillment of the prescription orders including instructions for management of the medication inventory database and prescription order data base and to minimize the cost function associated with fulfillment of the prescription orders stored in the prescription order database. The programmed instructions enable: (1) for each prescription within the prescription order, selection of the medication storage location from which to obtain the medication required to fulfill the prescription; and (2) for each prescription order, determination of a prescription sequence corresponding to the sequence in which each prescription is fulfilled, first to last, within the prescription order.

Once the sequence is determined, the control computer utilizes programmed instructions to permit the system to present in human-readable form (for each prescription order), the prescription sequence and the storage location of the medication comprising each sequenced prescription, and generate a print_label command following obtaining of each sequenced prescription. The print_label command is received by a label printer electronically connected to the control computer causing the label printer to print a label including prescription information and machine-readable indicia for each sequenced prescription. The label is of a type adapted for application to a container for each prescription within the prescription order.

The prescription sequence may be visually presented on a display device located at a work station in the pharmacy. More than one work station may be provided. An input device at the work station permits the pharmacist or filling technician to select each of the sequenced prescriptions for fulfillment. Preferably, the prescription sequence presented includes, for each sequenced prescription: text information; medication image information; and an icon representing each storage location corresponding to the sequenced prescription.

Preferably, a sequence sheet is provided as an aid to the pharmacy personnel in fulfilling the prescription order. The prescription sequence is printed at the pharmacy and includes the prescription sequence printed thereon including the machine-readable indicia for each sequenced prescription. The sequence sheet may then be manually carried to each storage location as directed by the prescription sequence.

Preferably, the print_label command used to initiate printing of the label is generated in response to agreement between an initiate_dispense signal and a medication_dispensed signal. The initiate_dispense signal is triggered by an input device, such as a touch screen display, bar code scanner, mouse or keyboard, before obtaining each prescription in the order. The medication_dispensed signal is generated during or after obtaining each prescription in the order, for example by the automated dispenser or by manually scanning a bar code on the package containing the medication.

It is very highly preferred that at least one of the WMS work stations includes a computer for validation of the prescription order before release to a customer. The computer is electronically connected to the control computer and the input device for that computer includes, at least, a reader device electronically connected to the workstation computer. The preprogrammed instructions for validating each prescription order at the work station include instructions adapted to: (1) receive a first validation signal generated by selecting, with the input device, a prescription from the prescription sequence presented on the display device; (2) receive a second validation signal generated by reading, with the reader device, the machine-readable indicia on the label applied to the container corresponding to each selected prescription; (3) determine agreement between the first and second validation signals; and (4) release the prescription order after agreement for each prescription is determined.

The invention may include a replenishment process managed by the WMS.

BRIEF DESCRIPTION OF THE DRAWINGS

FIG. 2A is a schematic diagram of exemplary medication storage locations taken along section 2A-2A of FIG. 2.

FIG. 3A is a schematic diagram showing a side elevation view taken along section 3A-3A of FIG. 3.

FIG. 3B is a schematic diagram showing a side elevation view taken along section 3B-3B of FIG. 3.

FIG. 3C is a schematic diagram showing a side elevation view taken along section 3C-3C of FIG. 3.

FIG. 3D is a schematic diagram showing a side elevation view taken along section 3D-3D of FIG. 3 showing a representative medication storage location.

FIG. 4 is schematic diagram showing a top plan view of a further embodiment of a pharmacy including a pharmacy workflow management system according to the invention.

FIG. 4A is a schematic diagram of exemplary medication storage locations taken along section 4A-4A of FIG. 4.

FIG. 5 is a schematic diagram of an exemplary computer network useful in practicing the pharmacy workflow management system according to the invention.

DETAILED DESCRIPTION OF PREFERRED EMBODIMENTS

Figure 1:
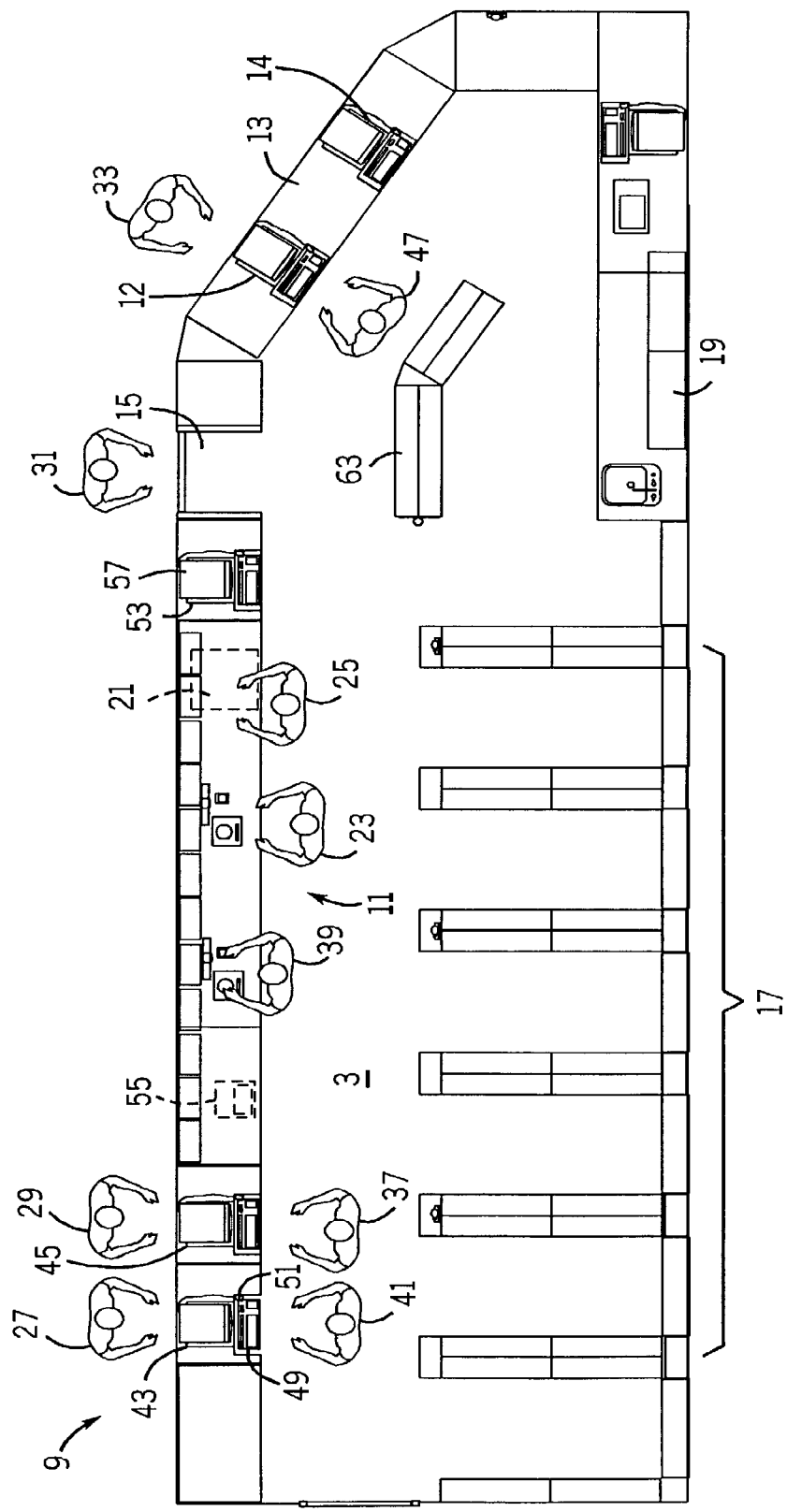
FIG. 1 is a schematic diagram showing a top plan view of a conventional pharmacy.
Figure 2:
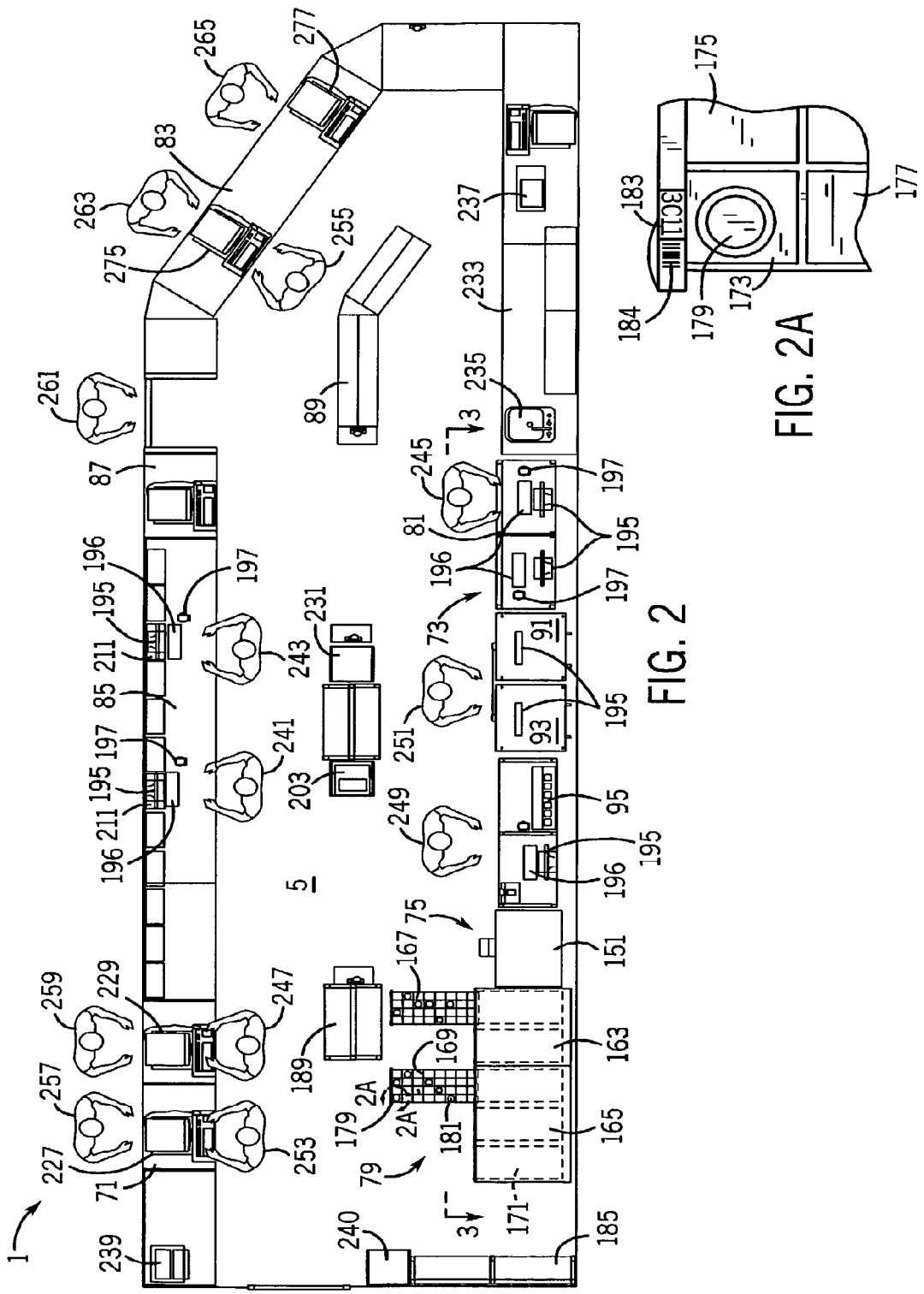
FIG. 2 is a schematic diagram showing a top plan view of a pharmacy including a pharmacy workflow management system according to the invention.
Figure 3:
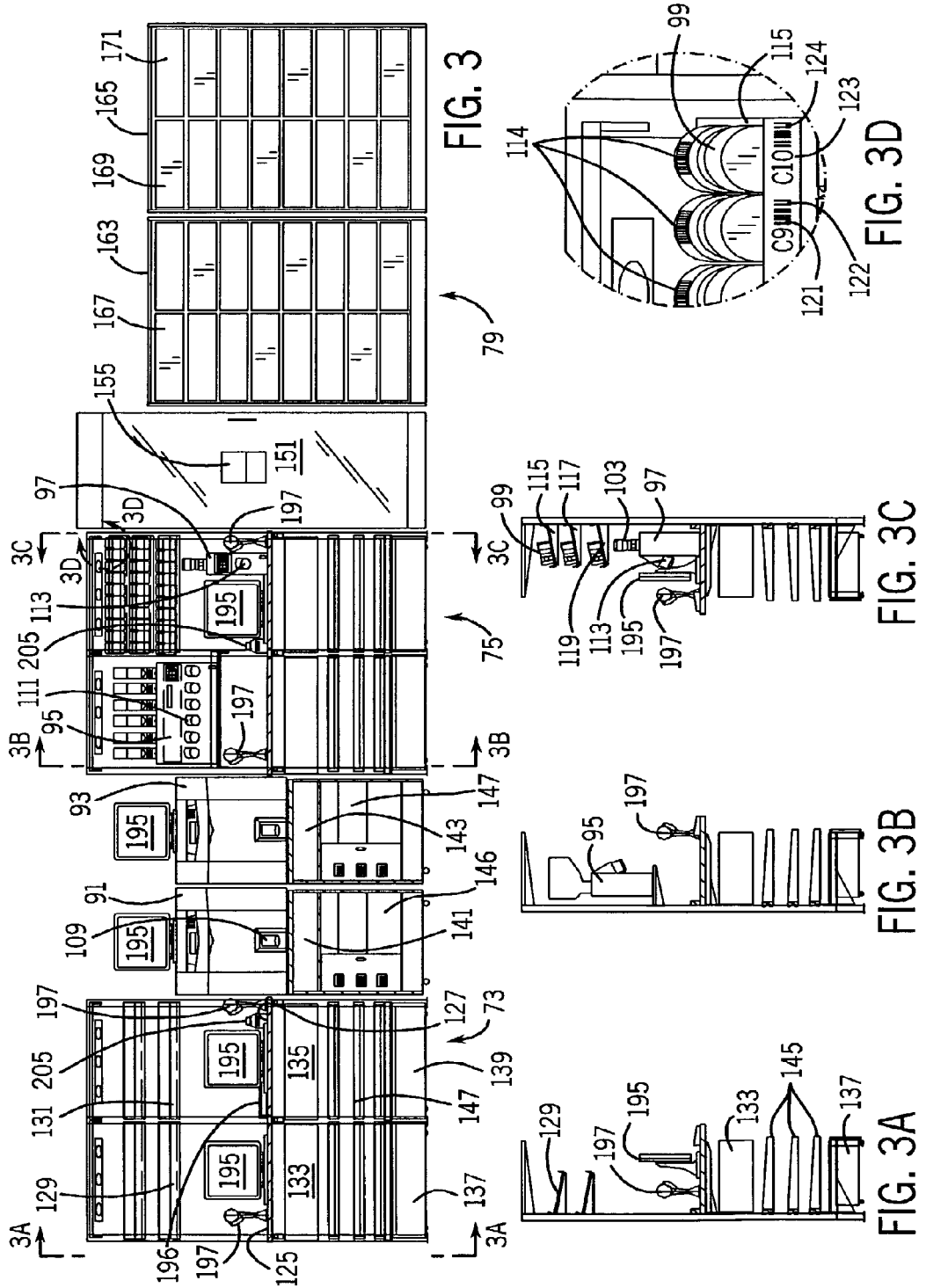
FIG. 3 is a schematic diagram showing a side elevation of components of the system of FIG. 2 taken along section 3-3 of FIG. 2.
Figure 6A:
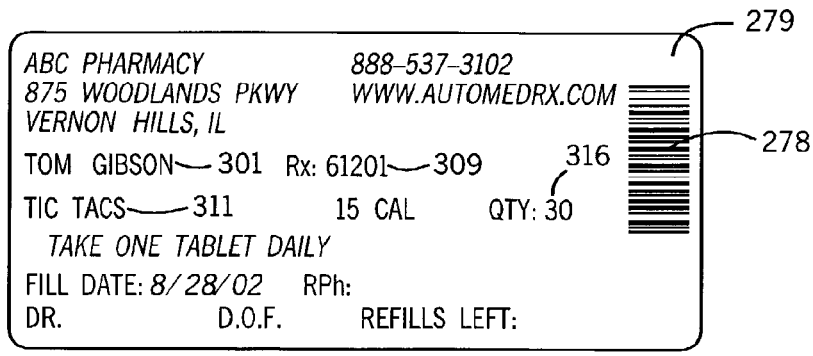
FIGS. 6A-6D are container labels provided in accordance with the invention.
Figure 6B:
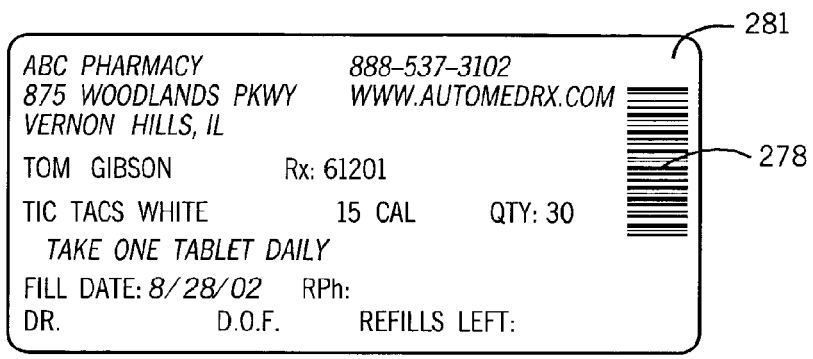
Figure 6C:
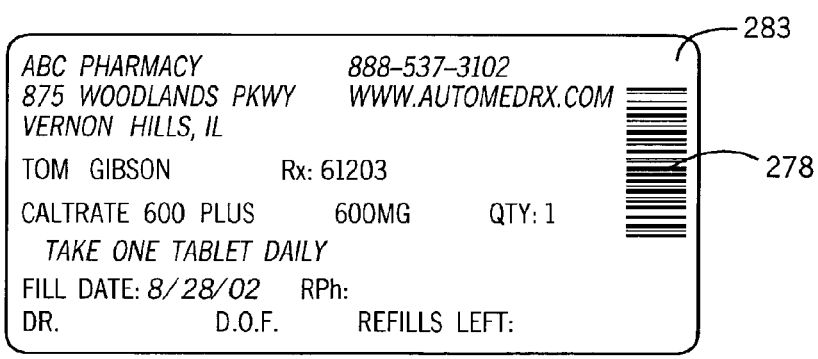
Figure 6D:
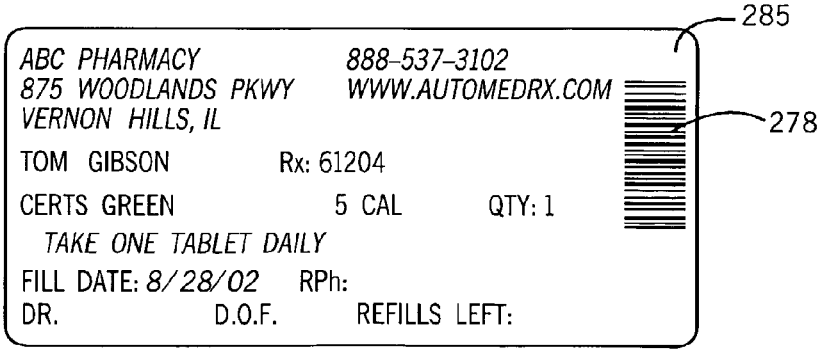

The pharmacy workflow management system 1 ("WMS") of the invention will first be described with respect to the exemplary pharmacy layouts illustrated in FIGS. 1-4. FIG. 1 represents the layout of a conventional pharmacy 3 while FIGS. 2-3 illustrate the layout of an improved pharmacy 5 according to the invention, including automated and non-automated (i.e., manual) dispensing apparatus as described in detail below. FIG. 4 shows a further improved pharmacy 7 according to the invention provided to demonstrate that the invention is highly adaptable for use with a variety of automated and non-automated dispenser apparatus. Each pharmacy 5, 7 shown in FIGS. 2-4 can be located in any environment wherein medications and products are dispensed in order to fill prescription orders and wherein direct human intervention in the order-filling process is required. Thus, the term "pharmacy" is intended to include diverse environments including retail pharmacies, pharmacies in alternate site facilities, hospital pharmacies and the like.

Referring now to FIG. 1, the conventional pharmacy 3 shown therein includes an order entry workstation 9, a filling/checking workstation 11, a payment workstation 13 and a consultation workstation 15. Conventional pharmacy 3 is provided with any number of non-automated storage locations at which medications and products are stored for access by pharmacy personnel. For example, the pharmacy 3 shown in FIG. 1 is provided with an array of six static storage shelf units 17. Each storage shelf unit within the array 17 is typically about 6 to 8 feet in height and includes a plurality of spaced-apart horizontally-oriented shelves. Medications and products are stored on each shelf within the array 17 pending manual retrieval for fulfillment of a prescription order.

Pharmacy 3 may include other storage locations such as a restricted-access cabinet 19 for storage of narcotics and other controlled medications. Pharmacy 3 may also include a refrigerator 21 for storage of perishable medications and articles.

Pharmacy 3 is staffed by personnel having varying levels of responsibility. The pharmacy staff includes at least one registered pharmacist 23, 25. Each pharmacist (e.g., pharmacist 23) is responsible for fulfillment of prescription orders and for verification of each prescription order before the order is provided to a customer 27-35. One or more filling technicians 37, 39 may be employed to assist pharmacists 23, 25 in fulfilling each prescription order. The pharmacists 23, 25 or filling technicians 37, 39 may also provide health-care-related information to a customer 31 at consultation station 15.

A data entry clerk 41 is provided to supply prescription order information to a host computer and pharmacy information system (not shown) via computer terminal 43 or 45 at data entry station 9. A sales clerk 47 processes sales transaction at the payment workstation 13 using computer terminal 14 or 16.

Workflow at conventional pharmacy 3 may be summarized in the following manner. Data entry clerk 41 may input the prescription order information to the system at data entry workstation 9 using keyboard 49 or computer mouse 51 of computer 43. Following adjudication by the pharmacy information system, each adjudicated order is held in a database on pharmacy computer 53 at filling/checking workstation 11 for fulfillment, typically on a first in first out ("FIFO") basis. Labels for attachment to each container associated with the prescription order may be printed on printer 55.

Pharmacist 23, 25 or filling technician 37, 39 selects the prescription order next in line to be filled. The prescription order, and prescriptions comprising the order, may be displayed on video display 57 associated with computer 53. The prescriptions making up the prescription orders are not arranged in any particular sequence.

Figure 7A:
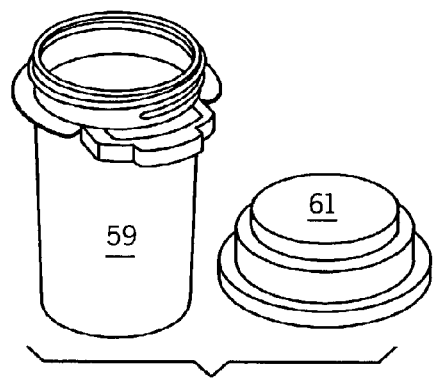
FIGS. 7A-7D are containers useful in practicing the pharmacy workflow management system according to the invention.
Figure 7B:
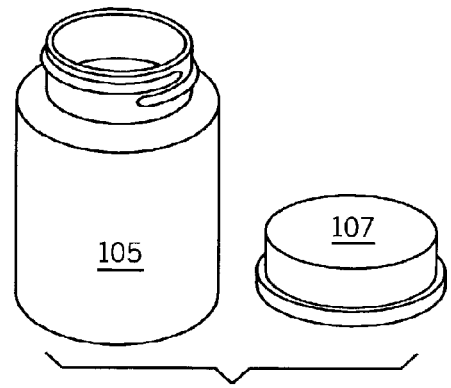

The pharmacist 23, 25 or filling technician 37, 39 then fills each prescription in the prescription order. Each prescription in the prescription order is filled by walking to one of the storage locations 17-21 and retrieving the appropriate medication which may be in bulk-form or in prepackaged form. The medication is then taken from the storage location 17-21 to the filling/checking work station 11 where the appropriate number of medications are metered into a container, such as vial 59 with reclosable cap 61 (FIG. 7A), in accordance with the prescription order. The corresponding label is placed on each container (e.g., vial 59).

This process is repeated until each prescription in the prescription order is fulfilled. The prescription order is then verified by pharmacist 23, 25 at filling/checking work station 11 to ensure that the correct medication is in each container (e.g., vial 59). The fulfilled order is then placed in a bag or other package and is held at a "will call" area 63 near payment work station 13. Sales clerk 47 processes the transaction and delivers the packaged prescription order to customer 33 at the payment work station 13.

There are a number of problems associated with conventional pharmacy 3 shown in FIG. 1 and described above. For example, conventional pharmacy 3 requires excessive amounts of time and spacial travel to access medications stored at the spaced apart storage locations 17-21. The pharmacist 23, 25 or filling technician 37, 39 must repetitively walk back and forth between storage locations 17-21 and filling/checking work station 11. In a busy pharmacy 3 this can amount to many miles of walking during a 40 hour work week. While known automation technology could be added to pharmacy 3 to facilitate dispensing of medications and products and improve accuracy of fulfillment, there is no process for organizing prescription order work flow so as to direct pharmacy personnel toward fulfillment of the prescription orders according to a minimized cost function. Therefore, there are opportunities for improvement of the pharmacy 3.

Referring next to FIGS. 2-5, there are shown pharmacies 5, 7 including the WMS 1 according to the invention. As will be explained in detail below, pharmacies 5, 7 are configured for improved management of prescription order fulfillment workflow. Pharmacies 5, 7 include many identical components and for purposes of convenience and brevity, identical reference numbers will be utilized to describe and identify these like components. Pharmacy 7 differs from pharmacy 5 primarily in that such pharmacy 7 is intended to fill a greater number of prescription orders per unit time (i.e., has a greater throughput) than the pharmacy 5 of FIGS. 2-3.

It should be understood that the pharmacies 5, 7 are exemplary. A pharmacy according to the invention may be scaled and tailored to meet the demands of the pharmacy operator. Thus, the WMS 1 may be adapted for use in retail, hospital and alternate site environments and such adaptability is an advantage of the invention.

As shown in FIG. 5, each pharmacy 5, 7 includes a local area network ("LAN") 65 which interfaces with a host computer 67 and pharmacy information system ("PIS") 69 and a number of designated areas at which pharmacy activities are carried out. FIG. 5 shows an exemplary LAN 65 for use in one embodiment of the invention. LAN 65 and its components may be adapted to meet the needs of particular pharmacy operators.

Pharmacies 5, 7 each include: an order entry point 71; one or more fulfillment centers 73-79 associated with medication storage locations as described below; validation point 81; and pick-up point 83. A technician work center 85 is provided as a general work area and as the primary area in which fulfillment of prescription orders is initiated. An optional consultation point 87 where advice and health-related information is provided may also be included as a part of pharmacies 5, 7. A will-call area 89 is provided to hold fulfilled prescription orders awaiting pick-up by the customer, health care worker or other designated person.

The novel fulfillment centers 73-79 will be described first followed by discussion of the interface of centers 73-79 with LAN 65 and other elements of pharmacies 5, 7. The automated and manual storage locations at which medications and products are stored and dispensed are organized into groups referred to herein as fulfillment centers 73-79. The number of fulfillment centers 73-79 and the apparatus associated with each such center may be adapted to meet the unique needs of each pharmacy operator. Pharmacy 5 includes three fulfillment centers 73, 75 and 79. In the example shown, first fulfillment center 73 is provided to dispense bulk-form medications via semi-automated dispensers 91, 93, 95 and 97. Bulk-form medications are medications that are in a loose, flowable form suitable for dispensing in any required quantity. Such medications may be provided in many different shapes and sizes and are dispensed into containers such as vials 59, bottles 105 and unit dosage packages 108 (FIGS. 7A-7D).

Dispensers 91, 93 are preferably FastFill® brand dispensers available from AutoMed Technologies, Inc. of Vernon Hills, Ill. Each FastFill dispenser 91, 93 dispenses from each of 64 bulk-form medication storage cassettes located within the dispenser. Dispensers 95, 97 are preferably QuickFill®Plus and QuickFill® brand dispensers also available from AutoMed Technologies. Dispenser 95 dispenses from six cassettes while dispenser 97 dispenses from 1 bulk-form medication storage cassette. All of the cassettes for dispensers 91-97 are interchangeable.

Figure 7E:
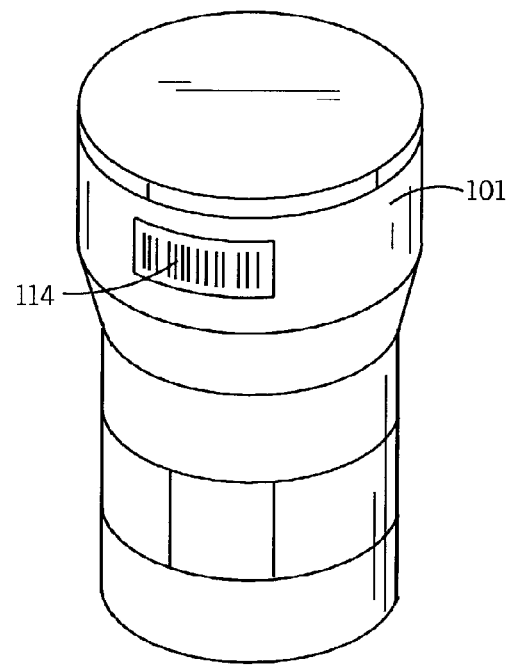
FIG. 7E is an exemplary cassette useful for storing bulk-form medications for dispensing by automated dispenser apparatus.
Figure 7C:
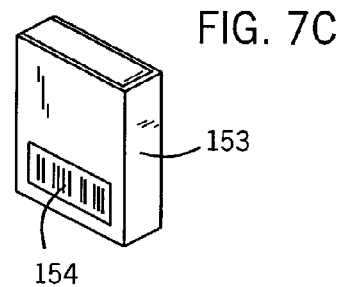

Cassettes 99-103 shown in FIGS. 3, 3C and 7E are exemplary of the type of cassette useful with dispensers 91-97. Each cassette 99-103 is designed to store a single type of medication in bulk form and is designed to fit on a corresponding base located on or within the dispensers 91-97. FIG. 3C shows cassette 103 mounted for use on QuickFill dispenser 97. The medications are metered out from the cassette corresponding to the medication designated for the prescription and into a container, such as vial 59 or bottle 105 (with reclosable cap 107). Each medication is dispensed into vial 59 or bottle 105 positioned in contact with a release gate (not shown) and below the appropriate dispenser spout, such as spout 109-113. Contact with the gate triggers the medication-_dispensed signal discussed below. Each cassette includes a code, such as a bar code 114 to facilitate location of each cassette at a storage location.

Each cassette (e.g., cassettes 99-103) is associated with a unique medication storage location, either in dispensers 91-97 or at a storage location, such as shelves 115, 117, 119 utilized when the cassettes are not positioned in or on the dispenser 91-97. Each storage location, for example shelf locations 115-119, has a unique storage location for each cassette (e.g., cassettes 99-103) represented by an address code of which codes 121, 123 are representative (FIG. 3D). Codes 121, 123 preferably include a machine-readable code, such as the bar codes 122, 124 shown as part of codes 121, 123 to further identify each unique storage location.

As shown particularly in FIGS. 3 through 3D, fulfillment center 73 of pharmacy 5 may optionally include additional work surfaces, shelves and drawers. For example, pharmacy 5 may include work surfaces 125, 127 and any number of additional storage locations provided to store medications and products useful in conjunction with fulfillment of prescription orders. Overhead shelves 129, 131 may be provided above work surfaces 125, 127. Large pull-out drawers, such as drawers 133, 135, pull-out foot drawers, such as drawers 137, 139 and lower tray shelves, such as shelves 145, 147 may be provided beneath work surfaces 125, 127. Base cabinets 141, 143 supporting dispensers 91, 93 may also include storage locations in the form of drawers, such as drawers 146, 147. Each of these storage locations has its own address code (not shown) to permit identification of the medications stored in a predetermined manner at the storage locations. If desired, the client computers 187-191 for fulfillment centers 73, 75 and 79 could be located in base cabinets 141, 143.

Figure 27:
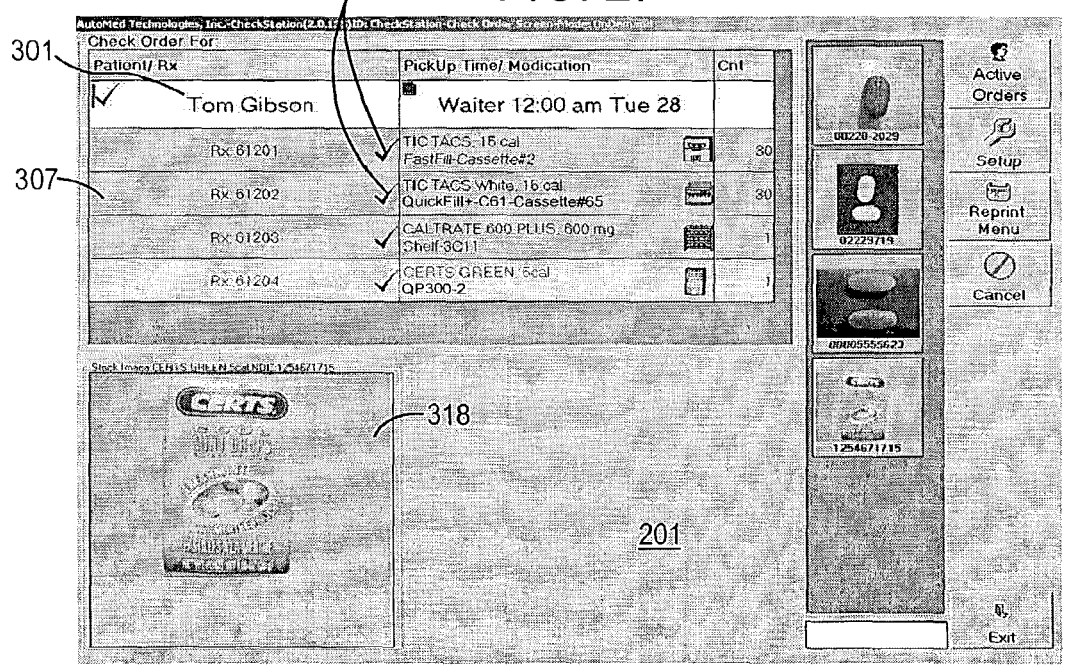
FIG. 27 is a front view of the screen image of FIG. 24 following validation of the entire prescription order. An enlarged reference image of the fourth prescription is provided. The order is ready to be released to the customer.

Referring further to FIGS. 2-3, pharmacy 5 may also include a further fulfillment center 75 including pre-packaged form automated product dispenser 151. A suitable dispenser 151 is a QP300 dispenser available from AutoMed Technologies. Pre-packaged form medications or products are products provided in the form of a pre-packed product, such as prepackaged product 153 shown in FIG. 7C or the CERTS container stock image 318 shown in FIG. 27. The prepackaged product holds a pre-determined quantity of a medication or product in a packaged form. Such a prepackaged product could include a wide range of articles and things such as a one-month supply (i.e., 30 units) of a medication, a prepackaged syringe or a packaged roll of gauze bandage. Frequently, there are cost advantages associated with prepackaging of medications into quantities commonly requested by customers such that it may be less expensive to fulfill a prescription order with a prepackaged medication product rather than to perform the dispensing through use of bulk-form medication dispensers at the pharmacy 5, 7. As discussed herein, WMS 1 permits selective dispensing between like medications based on the least expensive form of the medication available. The QP300 dispenser stores approximately 300 prepackaged articles at shelf locations within the device. The QP300 dispenses the designated prepackaged product (e.g., prepackaged product 153) into a bin 155 so that the product can be grasped by the pharmacist 241 or filling technician 247 Each prepackaged product 153 includes machine-readable indicia 154 (FIG. 7C), such as a bar code, and each storage location within the QP300 has a unique address associated with that location. The address may be in any suitable form and may consist of a code (including a machine-readable bar code) such as codes 121, 122, 123, 124 shown in FIG. 3D with respect to shelf 115 or code 183 shown in FIGS. 2A, 4A.

Referring to FIG. 4, pharmacy 7 includes a fulfillment center 77 which incorporates a QuickScript® brand automatic dispenser apparatus 159 in place of the automatic dispensers 91-97 and 151 provided for use in conjunction with pharmacy 5. The QuickScript dispenser 129 is also a product of AutoMed Technologies.

The QuickScript dispenser 159 has a higher throughput than the dispensers 91-97 and 151 and may be configured to dispense both bulk-form medications and prepackaged form medications. The canisters holding bulk-form medications (not shown) and prepackaged articles (e.g., prepackaged product 153) are positioned at unique storage shelf locations (not shown) within dispenser 159. Each storage shelf location has a unique address associated with it. The bulk-form medications are dispensed from the associated canister and are packaged into containers such as vial 59 or bottle 105 while the pre-packaged products (such as product 153) are stored in bins or at shelf locations (not shown) within dispenser 129. The address of each storage location may be in the form of a code 121, 122, 123, 124 shown by example in FIG. 3D with respect to shelf 115 or code 183 shown in FIGS. 2A, 4A.

Dispenser 159 is configured to automatically fulfill each prescription within a prescription order and then accumulate all medications and products pertaining to the prescription order in a single location, such as accumulator bin 161. A feature of dispenser 159 is that it can capture a digital image of the bulk-form medications after they are loaded into the container 59, 105 and before the associated cap 61, 107 is placed onto the container. The image can then be compared to a stock image 318 of the medication during validation as discussed in detail below. Stock image 318 is preferably held in a database associated with computer 209. Thereafter, the pharmacist or filling technician can collect all packaged medications and articles pertaining to the entire prescription order from the bin 161 for subsequent validation before being provided to the customer.

Pharmacies 5, 7 optionally include a further fulfillment center 79 consisting of manually-accessed high density shelf locations 163, 165. Each shelf location 163, 165 includes a plurality of drawers, of which drawers 167, 169 and 171 are exemplary. Each drawer (e.g., drawers 167-171) is mounted to slide outwardly from shelf locations 163, 165 as shown in FIGS. 2 and 4. Each drawer 167-171 optionally includes medication storage locations in the form of a plurality of cells, such as cells 173, 175 and 177 (FIGS. 2A, 4A). Each cell 173-177 is provided to store a medication or product, such as containers 179, 181 (FIGS. 2, 2A, 4, 4A). Each cell 173-177 has a unique address and may include an identification code 183. Code 183 may also include machine-readable indicia 184, 186, such as a bar code, to facilitate identification of each storage location.

Fulfillment center 79 of pharmacies 5, 7 may also include a static shelf unit 185 for storage of containers for bulk-form articles. Each static shelf unit 185 may be of any suitable height and includes a plurality of spaced apart horizontally-oriented shelves (not shown). The bulk-form medications or articles may be arranged in any suitable manner within shelf units 185. Refrigerator 240 for storage of perishable medications and articles may be provided at center 79. Further, a narcotic-product storage cabinet 189 may also provide storage locations within center 79. The narcotic-product storage cabinet 189 is locked with access limited to authorized personnel. As with each of the medication storage locations at fulfillment centers 73-79, each of the storage locations within shelf unit 185, refrigerator 240 and cabinet 189 is provided with a unique address which may be designated with a code (including a machine-readable bar code), such as codes 121, 122, 123, 124, 183, 184.

Each fulfillment center 73-79 is electronically connected to LAN 65 as shown schematically in FIG. 5. Each interconnecting solid line between the components of LAN 65 on FIG. 5 represents suitable electronic connection between such components. The dashed line connecting fulfillment center 77 to LAN 65 represents that center 77 is shown as part of pharmacy 7 and not pharmacy 5. In addition to one or more automated or manual storage locations, each fulfillment center includes a client computer, respectively designated by reference numbers 187, 189, 191, 193. Each client computer 187-193 is provided with a video display 195, and one or more input apparatus such as keyboard 196, a machine-readable code scanner 197, computer mouse 199 and touch screen 201. Because of the flexibility in configuration offered by LAN 65, it is possible that one display 195 may serve more than one center 73-79. For instance, display 195 at fulfillment center 75 could also serve as the display for fulfillment center 79. Each client computer 187-193 and associated components 195-201 at each fulfillment center 73-79 controls pharmacy workflow at that location. The client computers 187-193 are linked into the LAN 65 along with one or more printers, such as sequence sheet printer 203 and label printers 205.

The configuration of the overall system is, of course, dependent on whether the preferred mode of operation is "paperless" or will utilize a sequence sheet 269. Both from a perspective of convenience and from increased productivity, a system configured for paperless operation would include a greater number of video displays 195 positioned conveniently at each fulfillment center about the pharmacy. Other input devices, such as keyboards 196, machine-readable code scanners 197 and computer mice 199 are provided. For configurations utilizing a sequence sheet 269 and for reasons of both productivity and convenience in such a configuration, it would be necessary to provide machine-readable code scanners 197 at each fulfillment center.

The architecture of the computer system responsible for management of the pharmacies 5, 7 will now be described, particularly with respect to FIG. 5. Each of the client computers 187-193 of pharmacies 5, 7 is part of LAN 65 which interfaces these client computers to control computer 209. Client computers 211, 213 are located, respectively, at the technician work center 85 and the validation point 81. Computers 211, 213 include one or more input apparatus identical to computers 187-193 including a keyboard 196, a machine-readable code scanner 197, computer mouse 199 and touch screen 201. Client computers 187-193 are located, respectively, at or near fulfillment centers 73-79.

Control computer 209 is interfaced with host computer 67 of PIS 69. Host computer 67 is electronically connected to pharmacy control computer 209, through hubs 215, 217 and patch panel 219. Additional hubs 221, 223, 225 may be provided to electronically connect components of LAN 65 to control computer 209. Computer terminals 227, 229 at order entry point 71 are electronically connected in any suitable manner to host computer 67 as part of PIS 69.

Control computer 209 is also referred to as a "controller" because of its role in controlling the pharmacy workflow as described herein. However it should be noted that the term "controller" may include any suitable device including computer 209 or may comprise the entire LAN 65 within WMS 1.

An important advantage of the WMS 1 and its control architecture is that the system can be adapted to the unique needs of each pharmacy and can be modified as the needs of the pharmacy change over time. For instance, a retail pharmacy will tend to serve customers who require that medications be dispensed into vials 59 or bottles 105. The prescription needs of retail customers tend to be based on prescription medications required over extended periods of time, such as a week or a month. Apparatus such as the dispensers 91-97 and 159 are suitable for this purpose as described above.

Figure 7D:
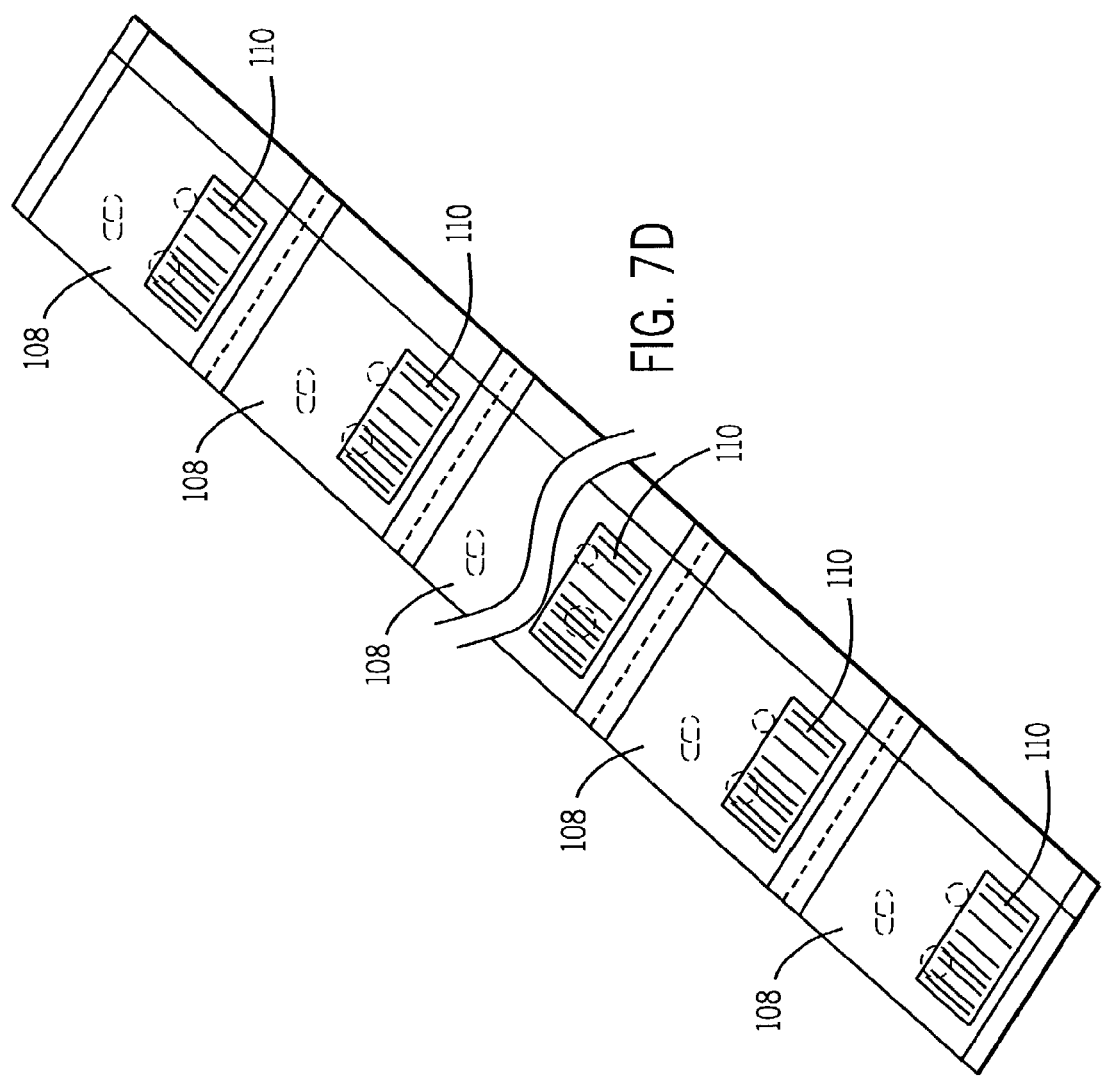

Hospitals or alternate site facilities, on the other hand, will tend to require dosage unit packages, such as packages 108, which are segregated into separate cells separated by perforation lines and organized into the package strip shown in FIG. 7D. Each of the packages 108 represent a dosage unit to be taken by the patient, for example, on a particular day or at particular times during the day. Each package includes machine-readable indicia 110, such as the bar codes shown, which identify all information necessary to match the medication to a particular patient. Other information, such as human-readable information identifying the patient name, medication type, instructions for taking the medication (such as the time of the day that the medication is to be taken) is typically printed on each package 108.

The package strip shown in FIG. 7D is of the type generated by an FDS brand automated dispenser (not shown) available from AutoMed Technologies. The FDS dispenser may easily be integrated into the WMS 1. WMS 1, therefore is easily adapted to serve the needs of the retail or hospital/alternate site pharmacy operator.

Moreover, if demand for medications at the retail and hospital/alternate site pharmacies should increase over time, any number of any number of additional dispensers, for example FastFill or FDS dispensers, could be added to the WMS 1 to address the changing needs of the pharmacy operator.

Referring further to FIGS. 2-4, the technician work center 85 shown therein is provided as a work area for initiating fulfillment of prescription orders and as a general work station. Technician work center 85 includes client computer 211 (or computers 211) and the associated display and input apparatus 195-201 described above. While a separate technician work center 85 is highly desirable, it should be noted that the function of center 85 could be performed at any client computer within LAN 65.

A sequenced prescription order is presented to the pharmacist 241 or filling technician 247 at the technician center 85 to initiate fulfillment. Specifically, the sequence in which the prescriptions are to be fulfilled is presented on video display 195 associated with technician center computer 211. It is highly preferred that the prescription sequence is also presented in the form of a "sequence sheet" 269 which is a paper record of the sequenced prescriptions shown on the display 195. The sequence sheet is printed before fulfillment of the prescription order and may be carried by the pharmacist 241 or filling technician 247 as she walks to the fulfillment centers 73-79 designated for fulfillment of the order. Sequence sheet 269 is preferably in the form of a tote bag into which each prescription is placed after fulfillment.

Sequence sheet 269, while highly preferred, is not required as WMS 1 may operate in a "paperless" mode. In the paperless mode, the sequenced orders are presented on display 195 at technician center 85 and on the displays 195 of each fulfillment center 73-79 accessed to obtain medications required by the prescription order. The pharmacist 241 or filling technician 247 merely follows the workflow path as directed by the arranged text and icon storage location information 313, 315.

Figure 30:
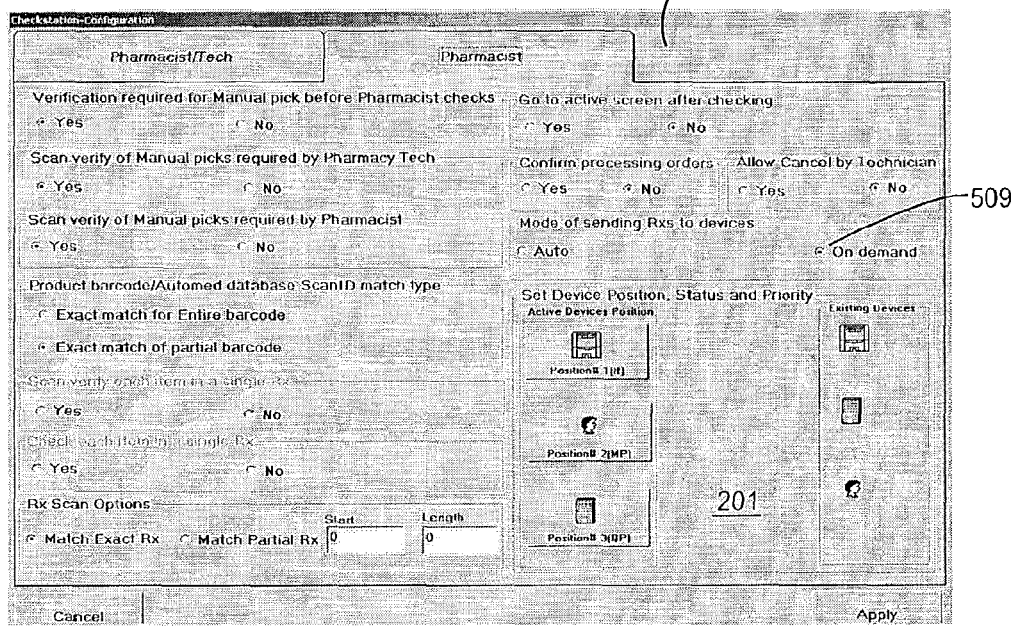
FIG. 30 is a front view of a further screen display showing additional system set up commands including selection commands for automatic and manual modes.

WMS 1 may be set in an automatic "automode" or in an "on-demand" mode using the mode selection control 509 provided on set up set up screen 510 (FIG. 30) presented on display 195 at technician center 85 or validation point 81. If the program is in automode then prescription orders are placed in a FIFO queue associated with the prescription order database 507 for fulfillment one after the other. The pharmacist 241 or filling technician 247 merely fulfills each prescription order in the sequence in which the prescription orders are presented to him by the queue. Therefore, WMS 1 advantageously reduces the need for human decision making in the order fulfillment process reducing potential errors and minimizing the cost function.

If on-demand mode is selected, the prescription orders are manually selected for fulfillment by the pharmacist 241 or filling technician 247 in the manner described below with respect to the method. Again, WMS 1 provides easily understood direction to the pharmacy personnel with respect to the most efficient manner of prescription order fulfillment.

Both the automode and on-demand mode may be modified by designation of the customer as a "waiter," meaning that the customer is waiting to pick up the medication. In such an instance, control computer 209 automatically places the prescription order for the waiting customer at the head of the list of pending orders. This modification occurs irrespective of whether automode or on-demand mode is selected. Further, the status of the prescription order is indicated to be that for a "waiter" as shown in FIGS. 10-11, 22-24 and 28 to alert the pharmacist 241 or filling technician 247 as to the status of the prescription order.

Typically, the status of the customer as a waiter is determined at the time the prescription order is placed for fulfillment at order entry point 71 and is part of the prescription order data supplied by PIS 69 to control computer 209. However, the status of the prescription order may be modified in WMS 1 by selecting priority button 329 and then modifying the status of the pending prescription order on a separate set up screen (not shown) by designating the prescription order as being for a waiter or as non-waiter. The ability to modify the status of the prescription order based on whether the customer is waiting permits the pharmacist 241 or filling technician 247 to immediately respond to the needs of the customer, thereby better serving the customer.

A holding area 231 at validation point 81 may be provided to hold prescription orders after fulfillment but before validation. A work area 233 and adjacent wash basin 235 may be provided as an area for preparation and mixing of medications. A photocopy machine 237 may optionally be provided as may a facsimile machine 239 to assist the pharmacy personnel in performing their duties.

Validation point 81 is a work area within pharmacy 5, 7 at which a pharmacist 241 validates the prescription orders. Validation point 85 includes a client computer 213 the associated display 195 and keyboard, scanner, mouse and touch screen input apparatus 197-201 described above with respect to the other client computers 187-193 and technician center computer 211. The function of technician center 85 may be performed at validation point 81. The function of validation point 81 within WMS 1 is described in detail below.

Order entry point 71 is a work area within pharmacy 5, 7 at which order information is accepted by clerk 253. A customer (e.g., 257 or 259) provides a written prescription to clerk 253 together with any other information required to initiate fulfillment of the prescription order. The information provided by the customer 257 will typically include the customer's name and address. The written prescription order provided by the customer 257 to the data entry clerk 253 includes the physician's name and, for each prescription within the prescription order, provides the type of medication prescribed, the medication dosage and quantity, the date prescribed, the physician's instructions to the customer, the number of refills allowed and whether a generic version of the medication may be substituted. Clerk 253 also obtains information from customer 257 with respect to his insurance coverage, co-payments and any other pertinent information relating to payment for the prescription order.

The prescription order information can be provided through direct interaction with customers or may be provided to clerk 253 via telephonic communication with a physician. Prescription order refill information may be provided to clerk 253 through any suitable means including via e-mail or computer interactive telephone communication also known as "IVR".

Computer terminals 227, 229 at order entry point 71 are provided to enter the prescription order information into the host computer 67 to which the terminals 227, 229 are electronically connected. (Terminals 227, 229 are identical and for purposes of brevity only terminal 227 will be discussed). Terminal 227 includes a video display 195 and keyboard, scanner, mouse and touch screen input apparatus 197-201. Typically, a window is provided on display 195 which includes data entry fields provided to prompt clerk 253 with respect to the information to be supplied by customer 257.

As described herein, PIS 69 resides on host computer 67 and includes the software program which is used to process a prescription order before release of the order for fulfillment by pharmacy 5, 7. It should be noted that in terms of prescription fulfillment process, what is required is a prescription which has been approved for fulfillment. Thus, the PIS 69 can be something as extensive as a nationwide network of interconnected pharmacies or something as minimal as an order entry station.

The prescription order information entered into host computer 67 is then adjudicated by PIS 69. Adjudication involves processing the prescription order to determine that the prescription order should be fulfilled and to determine whether any special processing is required. For example, insurance and co-payment information is typically confirmed. The customer's medical records may be searched to determine whether there are potential adverse drug interactions potentially at issue.

If the prescription order is compliant with the adjudication process then the prescription order is sent by the PIS 69 to the control computer 209 and into a prescription order database 507, preferably located on control computer 209. As described below in connection with the method, WMS 1 conducts a review of the received prescription order to determine whether the data is in the proper format and sequence and to determine whether the prescription order can be fulfilled by WMS 1. The adjudicated order is then available for subsequent processing at the technician center 85, fulfillment centers 73-79 and validation point 81. The signal representing the adjudicated order cleared for fulfillment consists of data in any suitable structure and format.

Pick up point 83 is an area in pharmacy 5, 7 where sales clerk 255 processes the prescription order and provides the fulfilled order to the customer, health care provider or other authorized person. Pick up point 83 is configured to meet the needs of the particular pharmacy. Pharmacies 5, 7 include computer terminals 275, 277 to process financial and customer information entered by sales clerk 255. Terminals 275, 277 may interface with PIS 69. Will call area 89 is a storage location for fulfilled orders awaiting processing at pick up point 83. Each prescription order at will call area 89 is held within a bin or shelf (not shown) organized by any suitable means, such as by the alphabetical order of the customer's surname. In place of a bin, the prescription orders may simply be held in the bag form sequence sheet for delivery to the customer.

Pharmacies 5, 7 are staffed by pharmacy personnel including at least one registered pharmacist 241, 243, 245 one or more filling technicians 247, 249, 251, an order entry clerk 253 and sales clerk 255. Pharmacists 241-245 are capable of processing all aspects of prescription order fulfillment including the provision of advice and information and the important order validation step described in detail below and required before release of the prescription order to the customer 257, 259, 261, 263 and 265. The filling technicians 247-251 are responsible for obtaining the proper quantity and type of medications and products from the storage locations at fulfillment centers 73-79 for fulfillment of the prescription orders. The filling technicians 247-251 are also able to perform order entry, inventory replenishment and the tasks of clerk 253. Filling technicians 247-251 are typically able to provide advice to customers 257-265. However, filling technicians 247-251 are not authorized to validate prescriptions or prescription orders, as only pharmacists 241-245 are authorized to perform this task. Order entry clerk 253 is responsible for order entry at point 71 and is authorized to perform the sales clerk's 255 tasks. Sales clerk 255 is authorized to process sales transactions at pick-up point 83.

Residing on control computer 209 is a software program 260 which includes pre-programmed instructions written to optimize the management of the pharmacy workflow, including the coordination of all mechanical and human resources of the pharmacy 5, 7 as described herein. Program 260 has access to a medication inventory database 513 adapted to describe the medications stored at each storage location associated with the fulfillment centers 73-79, including all non-automated and, if provided, automated dispensing devices 91-97, 151, 159. The medication inventory database 513 includes a complete description of each medication comprising the inventory. The description includes any suitable parameters selected by the operator such as the medication name, an identification number assigned to each medication, a stock image, NDC number, type of packaging, if any, and inventory quantity. The precise storage location is also associated with each medication. For example, the storage location may be a specified cassette within an automated dispenser (e.g., dispenser 91) or a row and shelf location of a static storage shelf (e.g. locations 121, 122, 183).

Program 260 further includes a prescription order database 507 adapted to store the prescription orders received from the PIS 69. Program 260 includes programmed instructions adapted to minimize the cost function associated with fulfillment of the prescription orders stored in the prescription order database. The programmed instructions enable: (1) for each prescription within the prescription order, selection of the medication storage location from which to obtain the medication required to fulfill the prescription; and (2) for each prescription order, determination of a prescription sequence corresponding to the sequence in which each prescription is fulfilled, first to last, within the prescription order. This optimization process and the various other steps carried out by program 260 to direct the workflow of the pharmacy 5, 7 are outlined in the method of operation described below.

As mentioned in the background section, a simple cost function to be minimized by program 260 may be the total time to fulfill a prescription order or the total spacial distance traveled by pharmacy personnel in order to fill a prescription order. For example, for each order consisting of more than one prescription, the optimization process which is undertaken determines the sequence by which the individual prescriptions in the order are to be filled in order to minimize the total length of time required to fulfill the order. This determination can depend on more than the distance that must be traveled to obtain each prescription, but also can include the time and cost required to count (e.g., manual counting versus automated counting versus prepackaged). Thus, for medications which may be stored in more than one form (e.g., prepackaged and bulk), the optimization process also includes the selection of which location from which to obtain such prescription medications in order to obtain the least expensive form of the medication, thereby minimizing the cost function.

In addition to total time or total distance traveled, other cost functions can be utilized in order to achieve certain desired optimum performance. For example, the sequence of a particular order and the selection of the locations from which medications are obtained can also be influenced by orders which are filled immediately prior to or immediately following the filling of such particular order. This is of course relevant to situations in which several prescription filling technicians 247-251 are working at the same time in a pharmacy 5, 7. For example, if a bulk-form medication dispensing location (e.g., 91, 93) is being used to fill one or more prescriptions, the optimization process may modify a sequence to "work around" such bulk dispensing or may direct the technician 247 to obtain a medication from an alternate location. In such a case, the cost function being minimized may be a more complex function of time, taking into account how filling times are affected by "neighboring" prescription orders. Alternatively, the cost function may be a combination of total time and a term or terms which penalize conflicts which may occur at storage locations. Note that with a cost function that takes into account "neighboring" orders, performance benefits are possible even with orders containing only one prescription if the pharmacy inventory stores some medications in more than one storage location.

Numerous other cost functions can be constructed to optimize the performance of WMS 1 by either penalizing or rewarding certain events or variables involved in the prescription fulfillment process. For example, in addition to time, distance traveled, and avoidance of simultaneous filling at the same location, the actual dollar cost of the medication to the pharmacy may be taken into account as well as the utilization of personnel, the need for inventory replenishment, and the special needs of the customer. Depending on the construction of the particular cost function chosen, the pre-programmed instructions would include all of the operational parameters and descriptive data required to evaluate such cost function. For example, in cases in which the filling times are used in the evaluation of total time, specific operational data on filling times would be included in the pre-programmed instructions of program 260.

The preprogrammed instructions of program 260 for selecting the medication storage location and for sequencing will most likely reside in code on the control computer 209. However, it is also possible that a portion of the program 260 could suitably be on other networked computers, for example a technician work center computer 211 or validation point computer 213 in LAN 65.

Steps other than the optimization process are described in detail in connection with the method. Such steps include tasks to facilitate the workflow such as presentation (in human-readable form) of each prescription order, the prescription sequence and the storage location of the medication comprising each sequenced prescription before and after the medications and products are retrieved and generating a print_label command causing a networked label printer, for instance printer 205, to generate an adhesive backed label 279-285 once a prescription has been fulfilled. The print_label command prompts the label printer (e.g., label printer 205) to generate prescription information 301, 309, 311, 316 and machine-readable indicia 278 for application to each label 279-285 for each sequenced prescription. The label 279-285 may then be applied to the container 57, 105 or pre-packaged article 153.

Method of Optimized Management of Pharmacy Workflow

The inventive system and method will now be further described, particularly with respect to the flow diagram of FIGS. 9A-9D and the screen display images of FIGS. 10-30. The method is explained in the context of fulfillment of a hypothetical prescription order for a fictional person named Tom Gibson at pharmacy 5. The four prescriptions comprising the hypothetical prescription order consist of "medications" in the form of candy or antacid rather than actual prescription medications or articles. It is to be understood that any medication or article stocked in the medication inventory may be dispensed according to the system and method. The flow diagram of FIGS. 9A-9D uses the terms "customer" and "patient" interchangeably as the WMS 1 may be used for any person requiring fulfillment of a prescription order from a pharmacy.

Figure 9A:
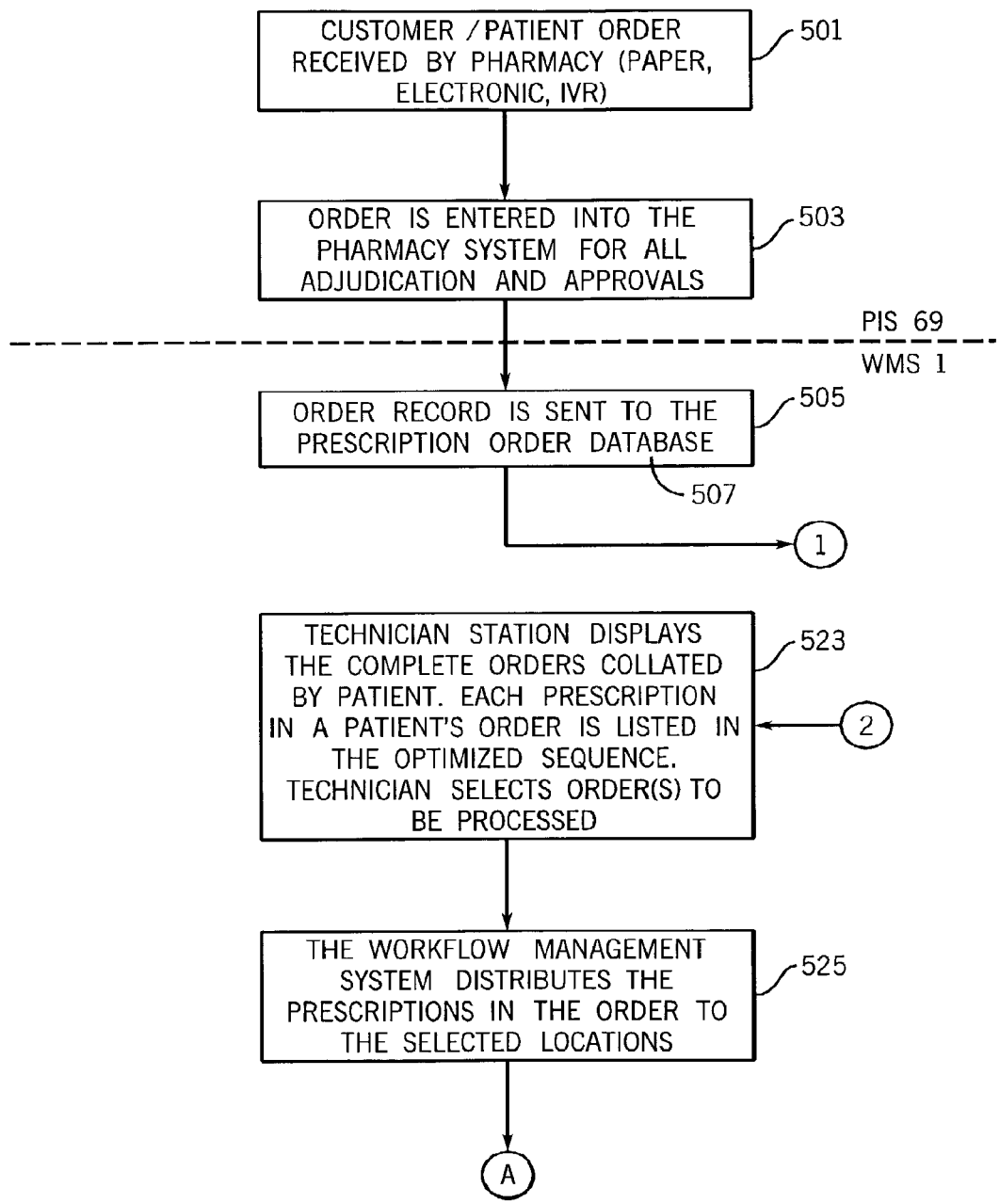
FIGS. 9A-9D provide a flow diagram describing a method of pharmacy workflow management according to the invention.
Figure 9B:
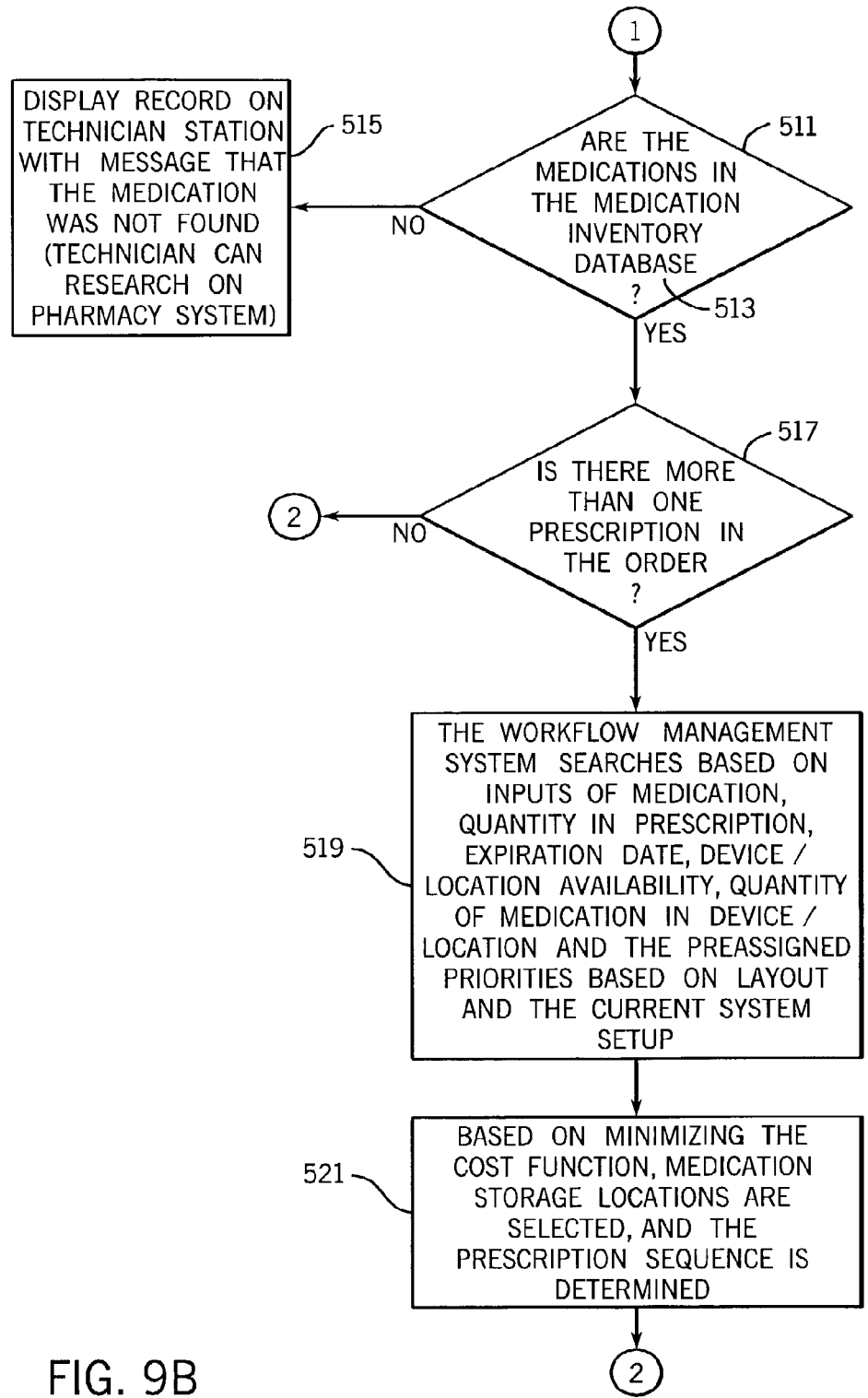

Referring then to FIG. 9A, the first two functional boxes of the flow chart are functions which take place within PIS 63 associated with host computer 67. Steps 501, 503 indicate the entry and adjudication of the prescription order. The order is received in any suitable form, typically at order entry point 71. The prescription order may, for example, be received in the form of a paper prescription, in electronic form or through IVR. The prescription order is adjudicated by means of the PIS 63 as described above.

All of the remaining steps to be described in FIGS. 9A-D represent functions carried out within the inventive WMS 1 in conjunction with control computer 209 and LAN 65 (FIG. 5) as represented by the demarcation lines in FIGS. 5 and 9A. In step 505, WMS 1 receives the adjudicated prescription order record from PIS 69 and the prescription order is entered into the prescription order database 507, preferably residing on control computer 209.

WMS 1 is set on one of two modes of prescription order fulfillment in a setup process (not modeled in the flow chart). The first mode is the automatic "automode" in which the prescription orders are automatically filled in a FIFO manner. The second mode is an "on-demand" mode which allows the pharmacist 241 or filling technician 247 to fulfill a prescription order immediately by manual selection of the specific prescription order presented on a display, preferably display 195 at technician work center 85. The ranking of prescription orders in WMS 1 may be modified based on whether the customer or patient is waiting for the medication as discussed elsewhere herein. The screen display images shown in FIGS. 10-28 represent WMS 1 processing the exemplary prescription order in the on-demand mode. Selection of the mode is made by the pharmacist 241 by selecting the appropriate setting 509 on set up screen 510 shown in FIG. 30.

Step 511 represents a check of the medication inventory database 513 to verify that WMS 1 is capable of fulfilling a particular prescription. Step 515 indicates that a negative response to step 511 has occurred and the pharmacist 241 or filling technician 247 is so informed. Step 515 reflects that a message (not shown) may be presented on display 195 at technician station 85 indicating that the medication could not be found. Specifically, the negative response step 515 would be triggered if the pharmacy 5 did not stock the type of medication required by the prescription order.

In step 517, WMS 1 determines that an optimization process is required if the prescription order contains more than one prescription. If the prescription order contains a single prescription, WMS 1 skips forward to step 523 discussed below. There is no minimization of any cost function which does not takes into account "neighboring" prescription orders when there is only one prescription in the prescription order.

If the prescription order includes multiple prescriptions, then WMS 1 commences step 519. In step 519, WMS 1 searches medication inventory database 513 and all applicable operational data, using all of the data which describes the prescription and the inventory, including the storage location of each medication, the quantity in inventory, the quantity required, the expiration dates, operational parameters and preassigned priorities. The search of step 519 is further based on the pharmacy layout (e.g., FIGS. 2-4) and the current system setup.

WMS 1 carries out the optimization process of the invention in steps 519 and 521. As described above, the optimization process results in the selection of the medication storage locations from which each medication will be obtained and the sequence in which fulfillment of the prescriptions comprising the prescription order will occur. Minimization of the cost function is the objective of the optimization steps 519, 521.

In step 523, the optimized prescription orders are displayed, preferably on display 195 at technician work center 85. The location from which each medication will be obtained is presented. The prescriptions 307 comprising the prescription order 305 are arranged in the sequence in which the prescriptions are to be fulfilled in order to minimize the cost function. Note that each order displayed has already been optimized according to steps 519-521.

Figure 10:
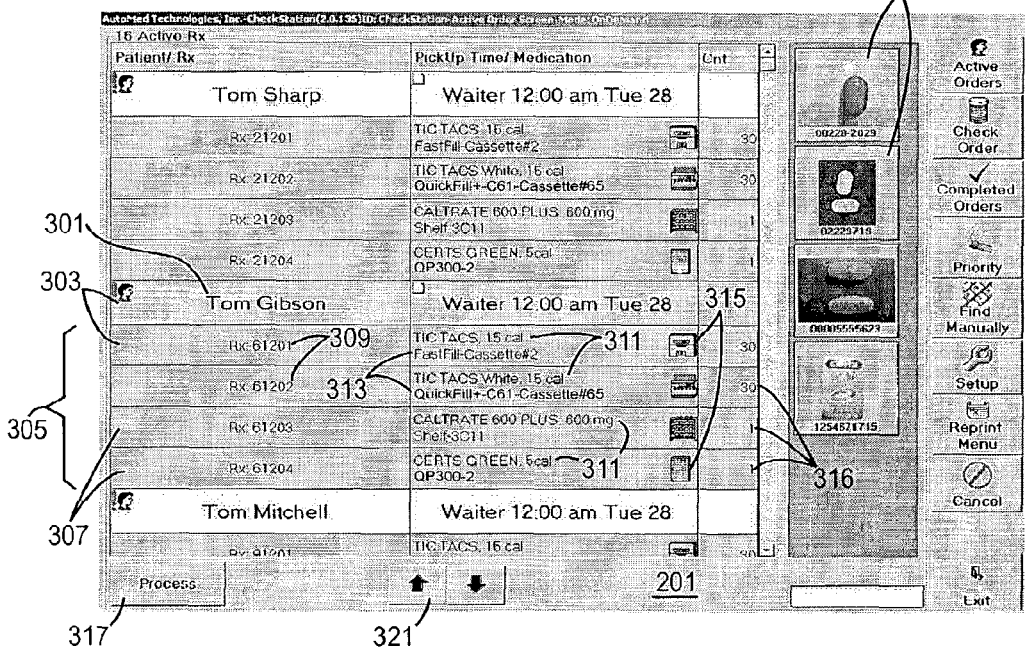
FIG. 10 is a front view of a video display screen image showing prescription orders pending with the system according to the invention.
Figure 11:
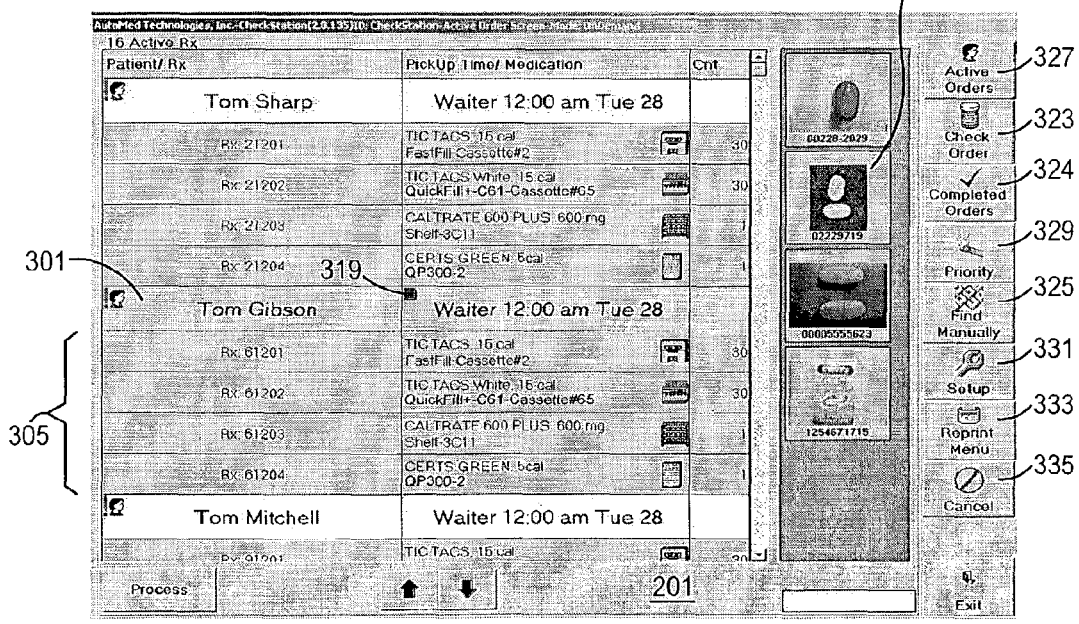
FIG. 11 is a front view of the screen image of FIG. 10 showing that the order for Mr. Gibson has been processed by the system according to the invention. The four prescriptions comprising Mr. Gibson's prescription order are presented in a sequence determined to optimize fulfillment and reduce the cost function.

FIGS. 10-11 show a series of exemplary screen image displays generated by WMS 1 on display 195 according to step 523. While it is preferred that step 523 take place at technician station 85, the step could take place using any video display electronically connected to LAN 65. Referring first to FIG. 10, that figure shows a queue of pending prescription orders organized by customer name and presented by WMS 1 according to step 523. The prescription order for Tom Gibson is one of the pending prescription orders in the queue. Mr. Gibson's name 301 is listed in the first row 303 of the prescription order 305 under the column for Patient/Rx. In the column for PickUp Time/Medication, Mr. Gibson is indicated to be waiting for the prescription order as of 12:00 a.m. on a Tuesday which is the $28^{th}$ day of the month.

Each prescription 307 comprising order 305 is listed in a separate row 303 beneath Mr. Gibson's name. The prescriptions comprising the prescription order have been placed in the optimized sequence generated in steps 519, 521. In the example shown, computer 209 has determined that the order is most efficaciously fulfilled by filling first from the apparatus at fulfillment center 73 followed by fulfillment at fulfillment centers 79 and 75, an example of routing the work flow around a center 75 that is busy fulfilling another pending order. The collection of prescriptions arranged in the optimal sequence is referred to herein as a "prescription sequence." Each prescription 307 includes a prescription number 309, a description of the medication in human-readable form 311, identification of the medication storage location of the medication by address 313 and icon 315 and the medication count 316. A stock image 318 of each medication corresponding to each prescription is provided.

The medication storage address 313 includes a text description of the exact cassette, shelf or other storage location where the medication is stored. For example, the TIC TACS for the first prescription are located in FastFill-Cassette #2 while the CALTRATE 600 Plus of the third prescription is located at Shelf-3C11. The icon 315 corresponds to one of the fulfillment centers 73, 75, 79 provided at pharmacy 5. For example, the icon 315 address corresponding to the first and second prescriptions in Mr. Gibson's order corresponds to fulfillment center 73 for dispensers 91-97, while the icons associated with the third and fourth prescriptions correspond, respectively, to fulfillment centers 79, 75 for storage shelf units 163, 165 and dispenser 151. The information associated with each prescription order is not limiting and may be tailored to meet the needs of the particular pharmacy operator.

As shown in FIGS. 10 and 11, pharmacist 241 or filling technician 247 selects Mr. Gibson's prescription order for fulfillment by touching the row 303 associated with Mr. Gibson's name followed by touching "Process" button 317 causing row 303 and the associated process box 319 to darken in color indicating the selection. Mr. Gibson's order may be located by scrolling up or down using touch arrows 321 or by searching for the customer name using a data entry field (not shown) presented on display 195 and accessed by touching the "Check Order" or "Find Manually" buttons 323, 325. Other optional buttons may be provided including an "Active Order" button 327 which causes WMS 1 to present a list of all pending prescription orders, a "Priority" button 329 which permits the pharmacist 241 or technician 247 to prioritize pending prescription orders for fulfillment (e.g., to designate a customer as a "waiter"), a "Setup" button 331 which permits access to setup screens (FIGS. 29, 30) to change the WMS settings, a "Reprint Menu" button 333 and a "Cancel" button 335 which cancels an action.

Returning to the method, in step 525 selection of a particular displayed prescription order (i.e., the order for Tom Gibson) causes WMS 1 to distribute the prescriptions to the selected medication storage locations in fulfillment centers 73, 75 and 79. Note that in automode, the distribution of prescriptions to the selected locations occurs in advance of the pharmacist preselecting a particular prescription order.

Figure 9C:
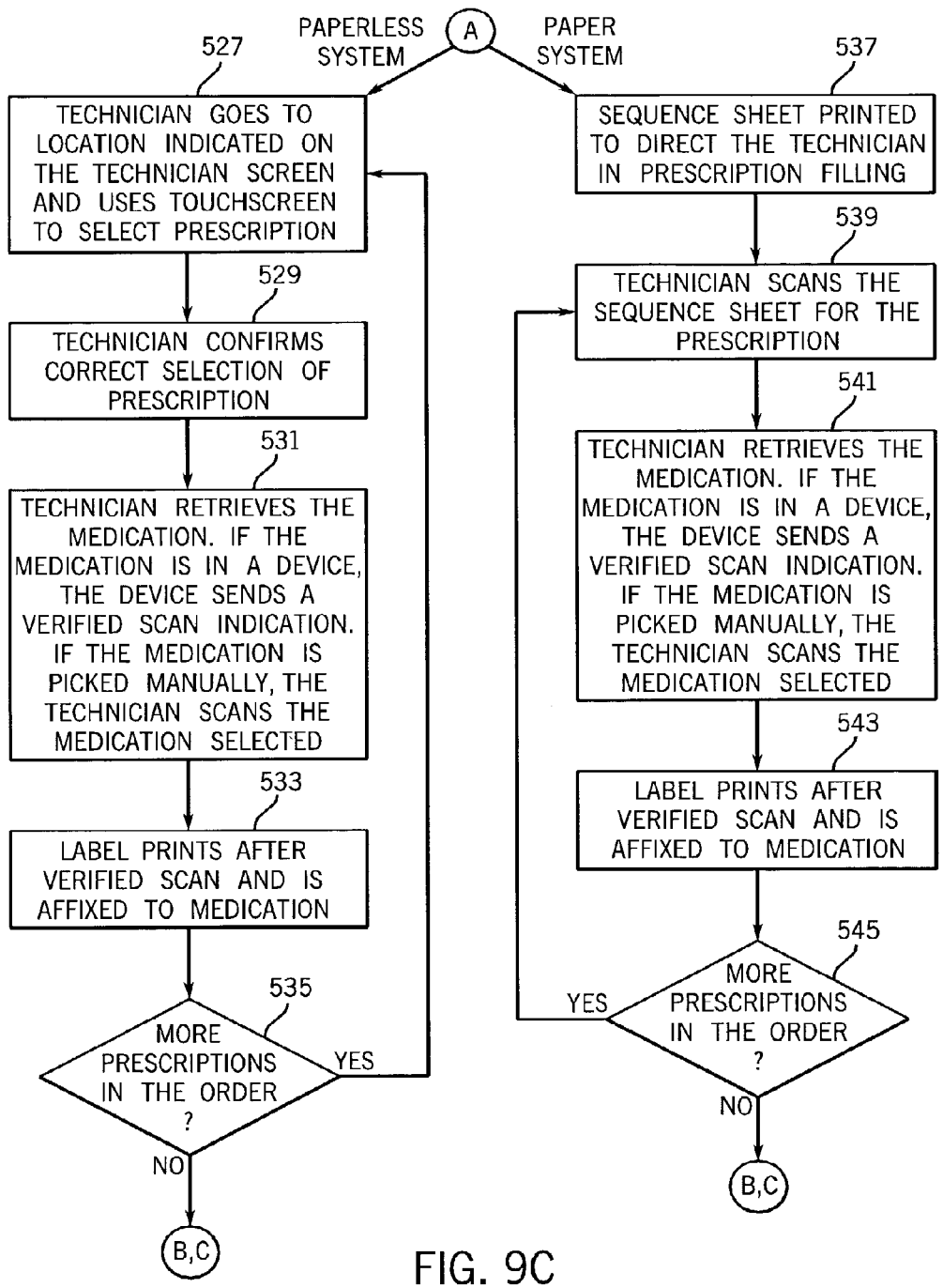

Referring next to FIG. 9C, fulfillment of the selected prescription order may occur in a paperless mode (steps 527-535) or in a mode utilizing a sequence sheet 269 (steps 537-545).

Figure 8:
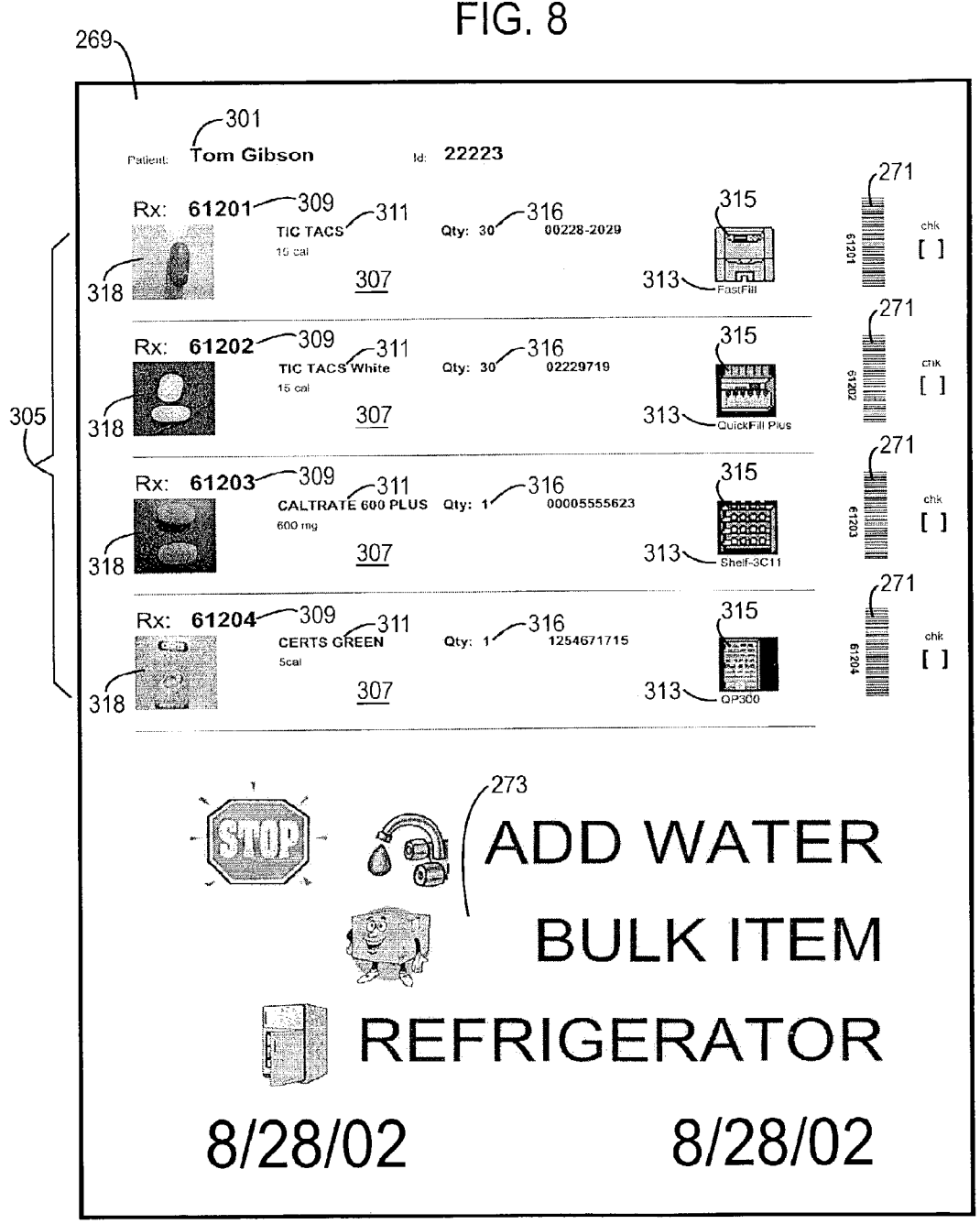
FIG. 8 is a sequence sheet in the form of a tote bag.

Referring first to the mode utilizing the sequence sheet 269, step 537 shows that a sequence sheet 269 (FIG. 8) is printed by printer 203 connected to LAN 65 and preferably controlled by control computer 209. Sequence sheet 269 is preferably a bag printed on one side by printer 209. It is intended that the sequence sheet 269 is carried by pharmacist 241 or filling technician 247 about the pharmacy 5 during collection of the medications pertaining to the prescription order. Sequence sheet 269 in effect acts as a "map" directing the pharmacist 241 or filling technician 247 along the most efficient path for fulfillment of the prescription order. The preferred bag-form of the sequence sheet 269 serves as a tote holding the fulfilled prescriptions during the process of prescription order fulfillment.

The prescription sequence is presented on sequence sheet 269 in the same arrangement as on the images displayed on the video display of step 523. (FIGS. 10-11). In addition to displaying all of the information shown on the video display 195 (FIGS. 10-11), sequence sheet 269 also includes machine-readable indicia 271, such as a bar code which corresponds to each prescription. Customer name 301, prescription number 309, prescription type 311 and address 313, 315 information for the order 305 may be provided. Additional information or instructions 273 may be printed on sequence sheet 269, including compounding instructions (e.g., "add water"), information about the medication packaging or special location information, such as storage in a refrigerator.

The sequence sheet 269 may be adapted for use as a "consulting" tool by including detailed information about each prescription in the order. For example, the sequence sheet could include text adjacent each prescription 307 with detailed instructions for taking the medication, such as the time of day the medication should be taken. Other detailed information might include information about potential side effects or drug interaction information. All of the prescriptions comprising the prescription order may be placed in the bag-form sequence sheet 269 and the entire bag could be provided to the customer at pick up point 83. Thus, the sequence sheet 269 would serve to package the prescription order and provide the customer with useful information about the prescription order.

Figure 12:
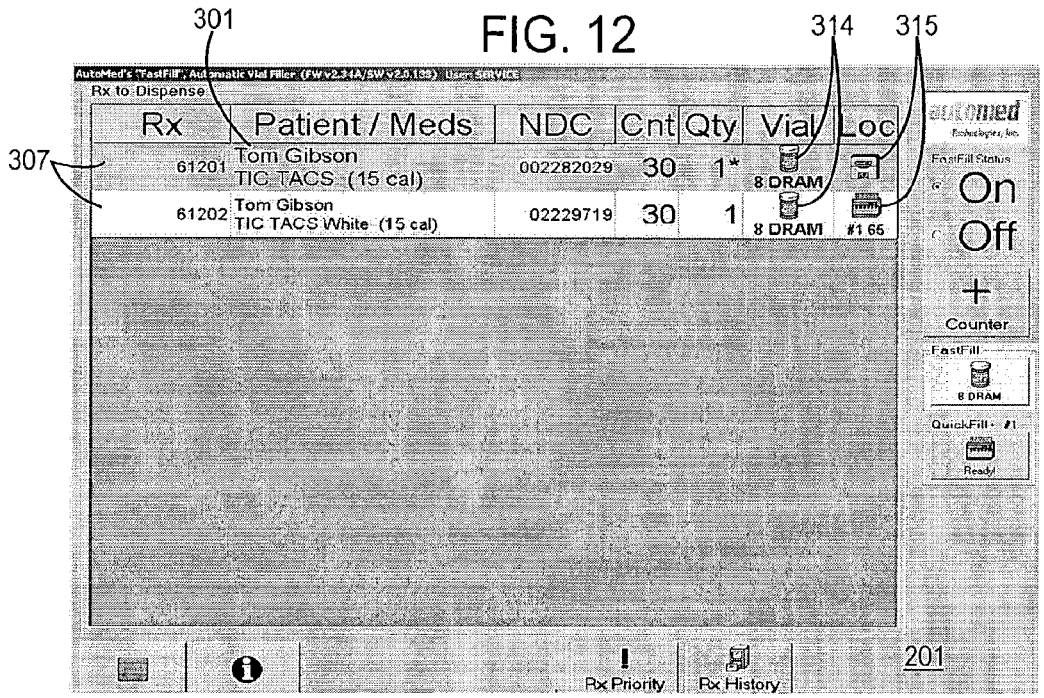
FIG. 12 is a front view of a screen image showing two prescriptions awaiting fulfillment by automated dispenser apparatus at a fulfillment center.
Figure 13:
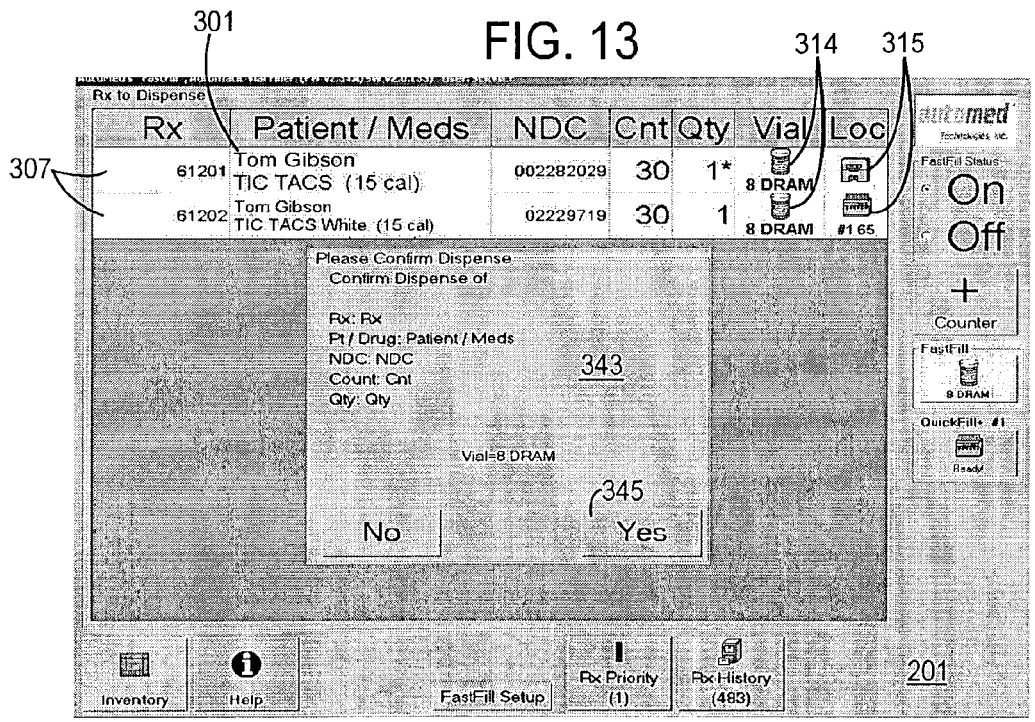
FIG. 13 is a front view of the screen image showing the pending prescriptions of FIG. 12 immediately prior to fulfillment of the first pending prescription, but in a paperless mode.

Also according to step 537, pharmacist 241 or filling technician 247 walks to the fulfillment center 73 associated with the storage location of the first among prescriptions 307 of the prescription order 305. In the prescription order for Mr. Gibson, the first and second prescriptions are to be fulfilled, respectively, from bulk-form medication dispensers 91 and 95, both of which are at fulfillment center 73 and are controlled by the same client computer 187 and display 195. As shown in FIG. 12, display 195 located adjacent dispenser 91 has presented thereon the two prescriptions to be dispensed, respectively, from bulk-form dispensers 91, 95. For purposes of consistency, the information for each prescription presented on display 195 at fulfillment center 73 corresponds to the information presented on the display of step 523 (FIGS. 10-11) and on sequence sheet 269. The display of FIG. 12 further provides container icon 314 directing the pharmacist 241 or filling technician 247 to select a particular type of container to hold the medication to be dispensed. In the example of FIG. 12, the containers pertaining to the first and second prescriptions are each vials 59 having an 8 DRAM capacity. The NDC number and prescription quantity are also presented on the screen represented by FIG. 12.

In step 539, pharmacist 241 or filling technician 247 utilizes a hand-held scanner 197 electronically connected to LAN 65 to read sequence sheet 269 bar code 271 associated with the first prescription. Scanning of the bar code 271 triggers generation of an initiate_dispense signal to control computer 209 which causes dispenser 91 to release the medication associated with the first prescription into a hopper or chute (not shown) within dispenser 91. The code 271 corresponds the prescription number 309 and is a unique identifier of the prescription 307. Therefore, the code 271 essentially points to all of the information associated with the prescription 307 including, for example, customer and prescription order identification, and the type, strength and quantity of medication to be dispensed. Control computer 209 (or another computer within LAN 65) activates the appropriate medication storage location (e.g. a cassette such as cassette 99-103) within dispenser 91 based on information within the medication inventory database 513 and meters the appropriate quantity into a hopper or chute in dispenser 91 in preparation for dispensing into vial 59.

In step 541, the empty vial 59 is placed under a spout 109, and the medication is dispensed into the vial 59. For the dispensers 91-97, the act of manually lifting a gate (not shown) near spout 109 triggers the medication_dispensed signal and causes the dispenser to dispense the medication into the vial 59. The medication_dispensed signal informs control computer 209 that the medication has been dispensed in the proper quantity. Typically, if the quantity is incorrect an error signal is generated to inform the pharmacist 241 or filling technician 247 thereof. The aforementioned process will vary depending on the type of automated dispenser being utilized. For example, the medication_dispensed signal may occur without human intervention in the dispensing process.

In step 543, a print_label command is generated by control computer 209 in response to this agreement between the initiate_dispense and medication_dispensed signals. This process along with the controlled management of the medication inventory ensures that the correct medication at the correct quantity and strength is matched to the correct customer, thereby significantly reducing potential for error. The print_label command causes label printer 205 to generate a label 279 corresponding to the first prescription and including the customer name 301 and prescription number 309, the type 311 and quantity 316 of the medication, the physician who prescribed the medication, the fill date and other information, such as the number of permitted refills. Label 279 is adhesive-backed and is manually placed on vial 59 by pharmacist 241 or filling technician 247. The vial 59 may then be placed in the bag-form sequence sheet 269.

Figure 14:
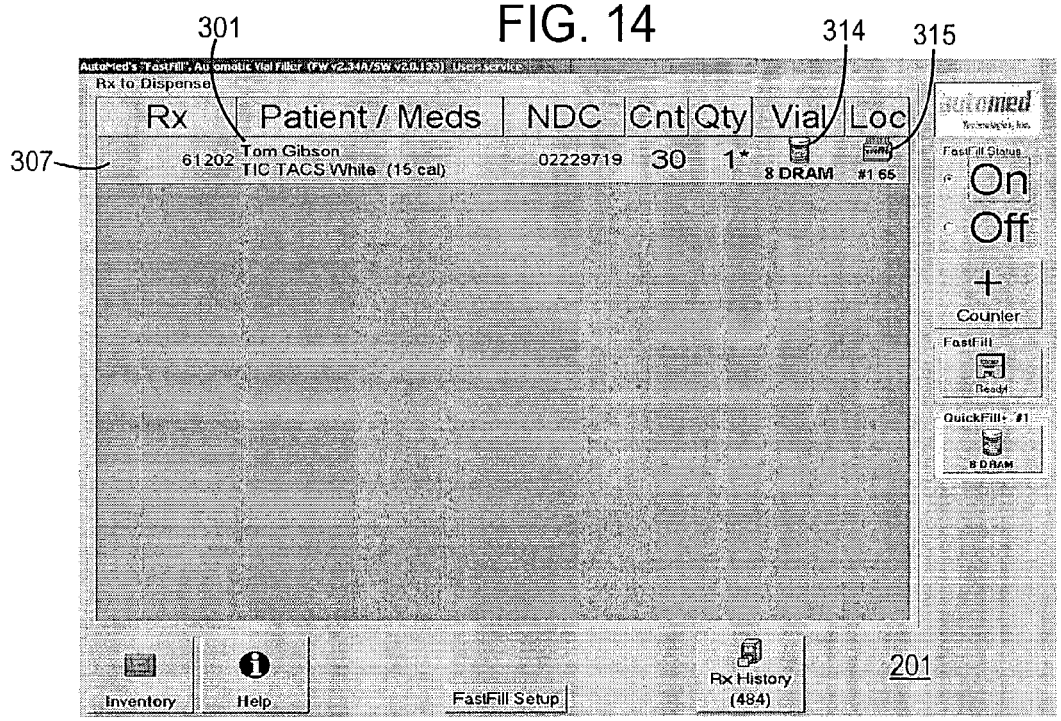
FIG. 14 is a front view of the screen image of FIG. 12 following fulfillment of the first prescription and immediately prior to fulfillment of the second prescription.
Figure 15:
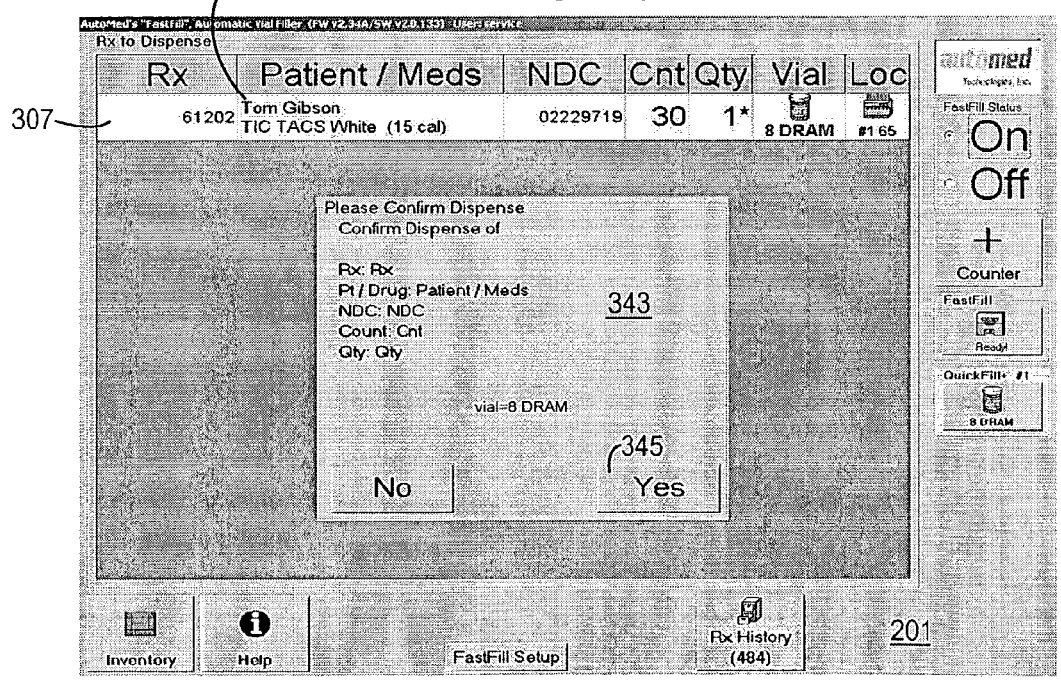
FIG. 15 is a front view of the screen image showing the second pending prescription of FIG. 14 immediately prior to fulfillment of such second prescription, but in a paperless mode.

According to step 545, steps 537-543 are repeated if the prescription order includes more than one prescription. With respect to the prescription order for Mr. Gibson, FIG. 14 shows the state of display 195 following dispensing of the first prescription but before dispensing the second prescription from bulk-form dispenser 95. The prescription information for the first prescription is deleted because that prescription has been fulfilled. Steps 537-543 are then repeated as described above resulting in dispensing of the medication for the second prescription from dispenser 95 through a spout (such as spout 109) and into a vial, such as vial 59. Label 281 is printed by printer 205 for attachment to vial 59.

Figure 16:
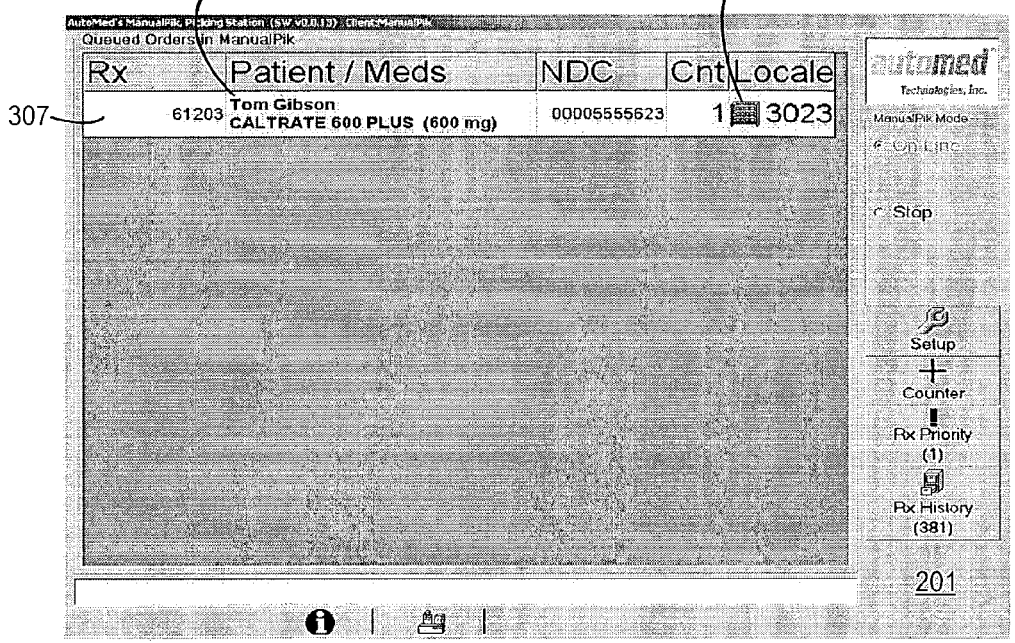
FIG. 16 is a front view of a screen display showing one prescription awaiting fulfillment by manual retrieval from a non-automated, manual shelf location.
Figure 17:
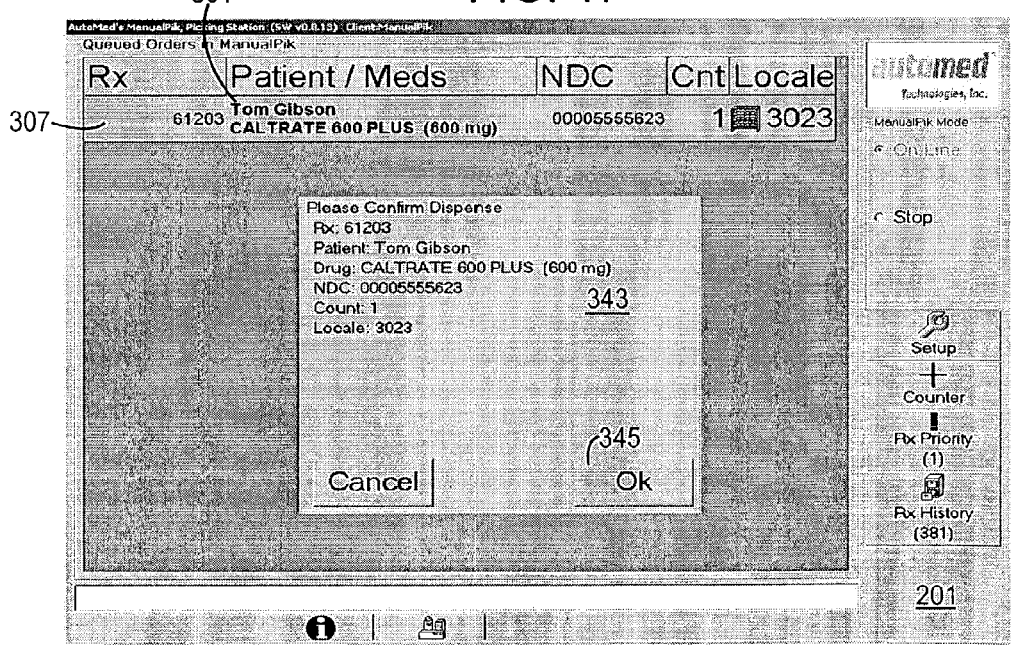
FIG. 17 is a front view of the screen image showing the pending prescription of FIG. 16 immediately prior to fulfillment of such prescription, but in a paperless mode.

The third prescription in Mr. Gibson's order is to be filled at fulfillment center 79 utilizing manually-accessed shelves 163, 165 as indicated by the storage location information 313 and icon 315 on the sequence sheet 269 and stock image information 318 on FIGS. 10-11 and 16. FIG. 16 is the image presented by WMS 1 on shared display 195 serving fulfillment centers 75, 79 adjacent to shelves 163, 165. FIG. 16 shows the single prescription 307 assigned for fulfillment at shelves 163, 165. FIG. 2A shows the storage location code 183 and cell 173 for container 179 which holds the CALTRATE 600 called for by the prescription order 305.

Figure 18:
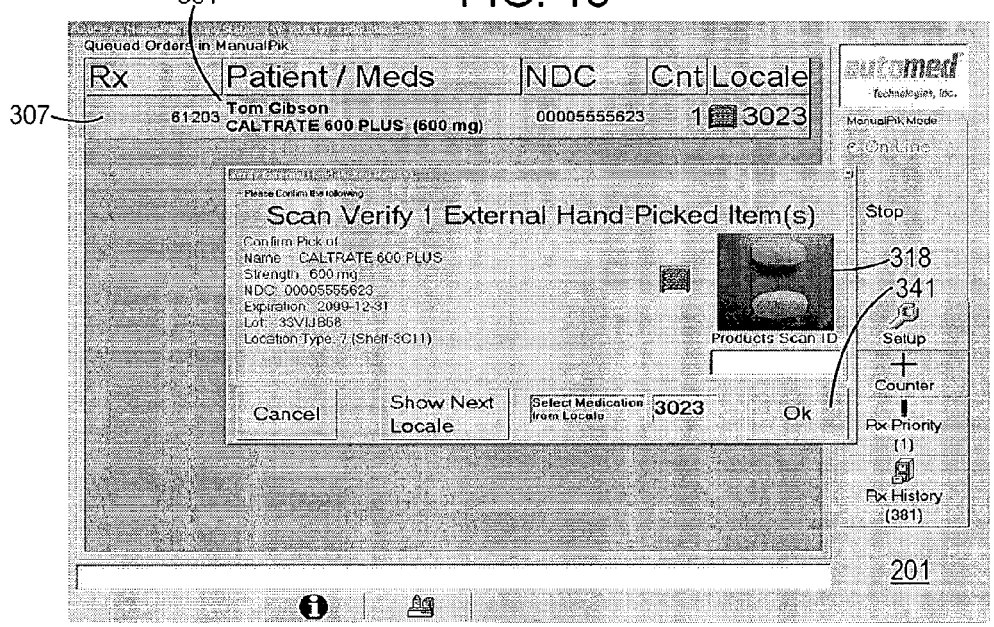
FIG. 18 is a front view of the screen image of FIG. 17 but showing an optional touch screen panel for confirming fulfillment of the pending prescription.

Steps 537-543 are repeated as described above resulting in manual selection of container 179 holding the CALTRATE 600 product. Fulfillment of the third prescription differs only from steps 537-543 in that the medication_dispensed signal is generated by reading (with scanner 197) a bar code (not shown) on the container 179 for the CALTRATE 600 product. Additionally, label 283 is printed for attachment to the container 179 for the CALTRATE 600 product. As shown in FIG. 18, a message box 337 may be presented on display 195 at center 79 presenting a stock image 339 and permitting verification of the manually-picked product. Selection of the "Ok" button 341 following visual comparison of the stock image 318 and medication completes the process of fulfillment of the third prescription.

Figure 19:
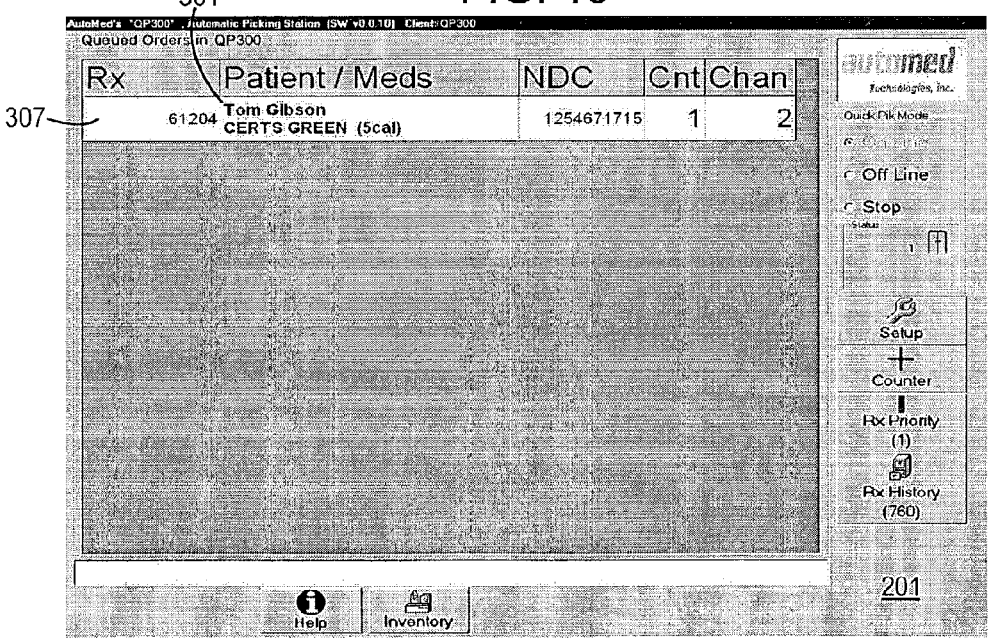
FIG. 19 is a front view of a screen image showing one prescription awaiting fulfillment by an automated unit-of-use dispenser apparatus.
Figure 20:
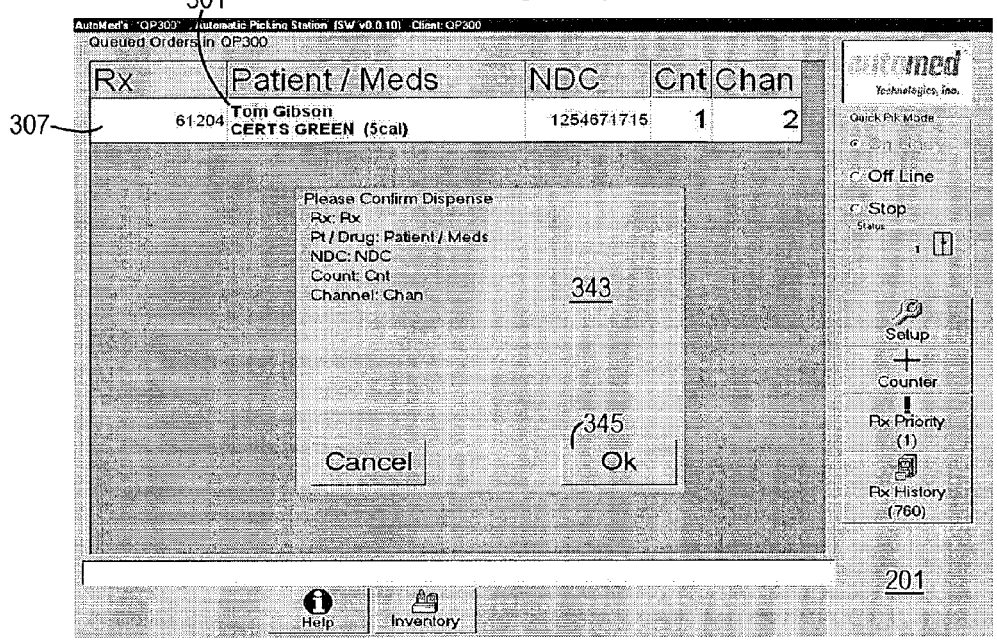
FIG. 20 is a front view of the screen image showing the pending prescription of FIG. 19 immediately prior to fulfillment of such prescription, but in a paperless mode.
Figure 21:
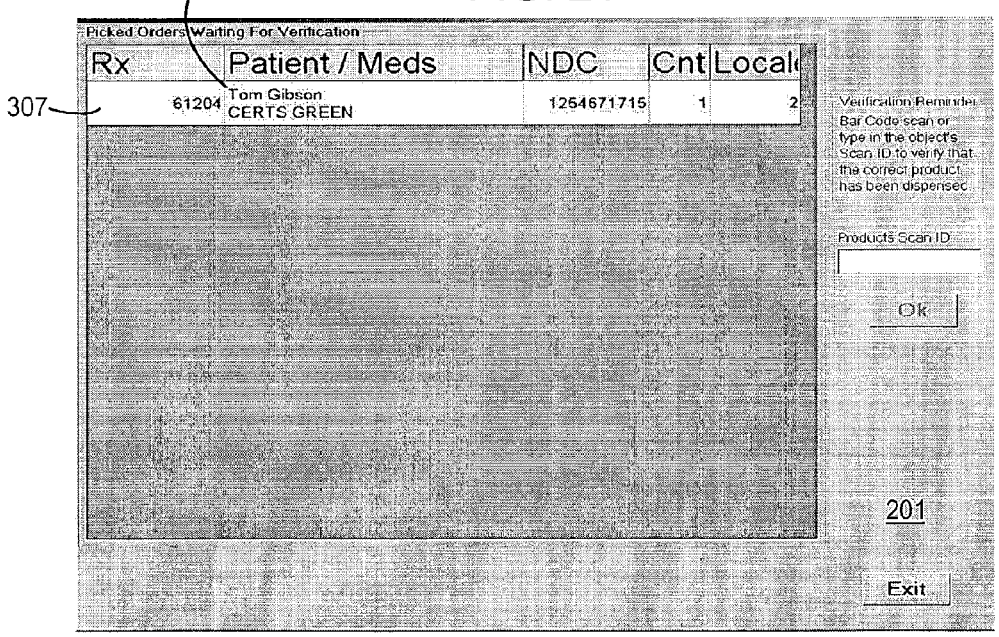
FIG. 21 is a front view of the screen image of FIG. 19 but showing an optional touch screen panel for confirming fulfillment of pending prescription.

The fourth prescription in Mr. Gibson's order is to be filled at the fulfillment center 75 automated pre-packaged article dispenser 151 as shown by the storage icon 315 on the sequence sheet 269 and icon information 315 on FIGS. 10-11. FIG. 19 is the image presented by WMS 1 on display 195 located adjacent to center 75 and dispenser 151.

Steps 537-543 are repeated as described above resulting in dispenser 151 dropping the package (such as package 153) containing the CERTS product into bin 155. Like fulfillment of the third prescription, the medication dispensed signal is generated by reading (with scanner 197) a bar code (e.g., bar code 154) on the package (not shown) for the CERTS product. Additionally, label 285 is printed for attachment to the pre-packaged container for the CERTS product. All containers for the four prescriptions may then be forwarded to the pharmacist for validation as described below.

The paperless system of steps 527-535 will now be described with respect to FIG. 9C. According to step 527, the pharmacist 241 or technician 247 walks to the center 73 associated with the first prescription order as shown in FIGS. 10-11. No sequence sheet 269 is provided or needed in the paperless system. The pharmacist 241 or filling technician 247 then touches the display 195 touch screen 201 adjacent the customer's name 301 causing step 525, the distribution step, to occur (FIG. 11).

In step 529 of the paperless system, a prompt 343 is generated after selection of the desired prescription as shown in FIGS. 13, 15, 17 and 20. Selection of the "Yes" or "Ok" button 345 confirms correct selection of the prescription and generates the initiate_dispense signal. Steps 531-533 of the paperless system are identical to steps 541 and 543 of the mode using the sequence sheet and the description of such steps for each of the four prescriptions comprising the Gibson prescription order is incorporated herein by reference. All of the fulfilled prescriptions are then forwarded to the pharmacist for validation as described below.

Figure 9D:
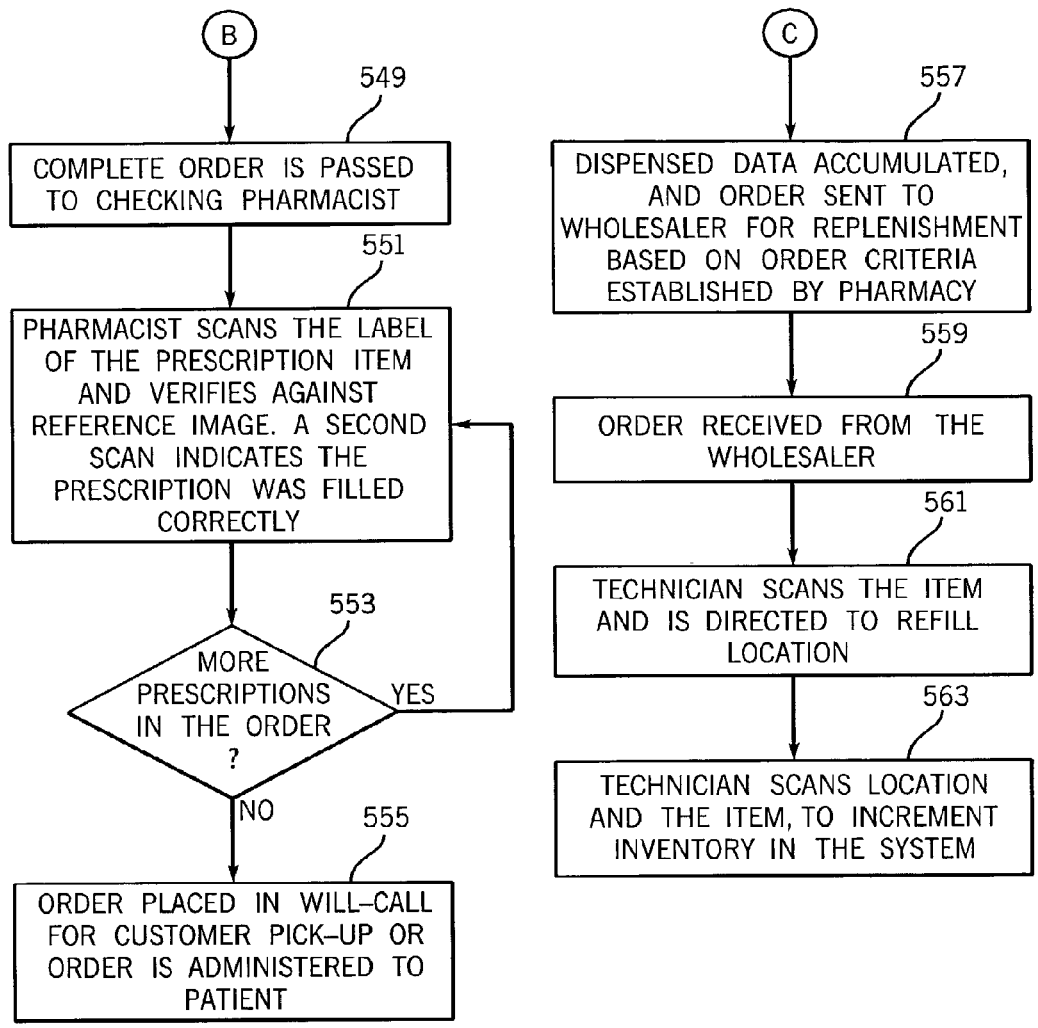

Validation of the prescription order 305 is represented by steps 549-555 on FIG. 9D. Validation is the review process wherein each prescription comprising the prescription order is inspected to ensure that the prescription order has been fulfilled correctly and in accordance with the prescription order. Validation includes, for example, confirmation that the prescription order is matched to the correct customer, confirmation that all prescriptions within the prescription order have been fulfilled and confirmation that the correct medication has been matched to each prescription. Validation may be accomplished through program 260 or through a separate software program residing, for example, on validation point computer 213 or on control computer 209.

Figure 22:
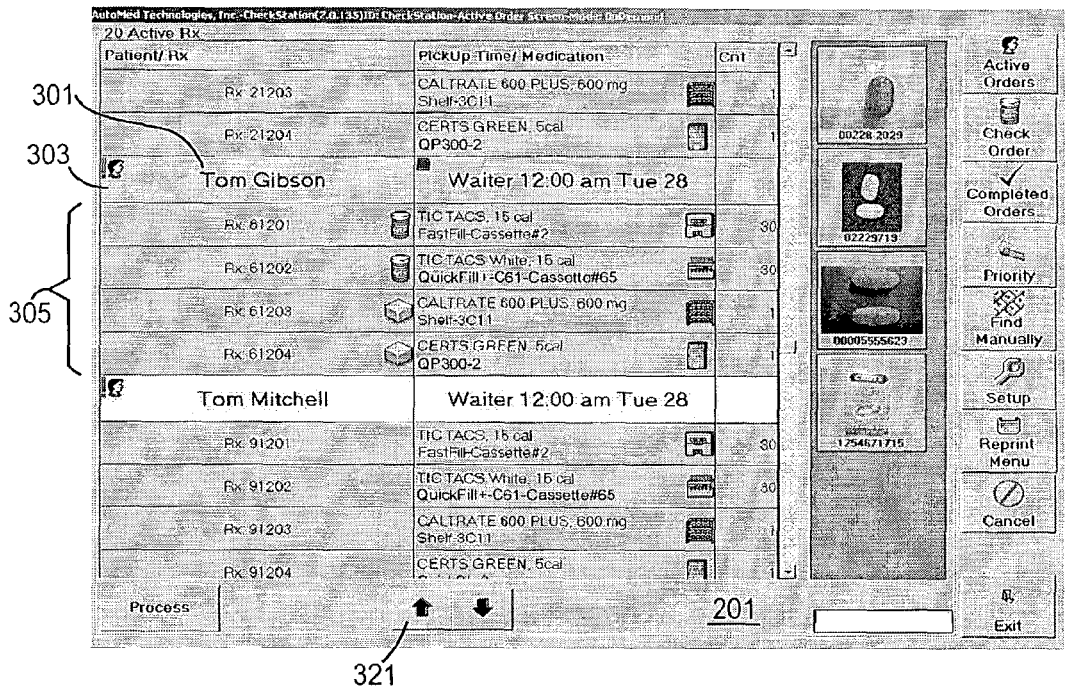
FIG. 22 is a front view of a screen image showing the four filled prescriptions comprising the prescription order prior to validation of the prescription order by the pharmacist. Reference images of the four medications comprising the prescription order are provided.
Figure 23:
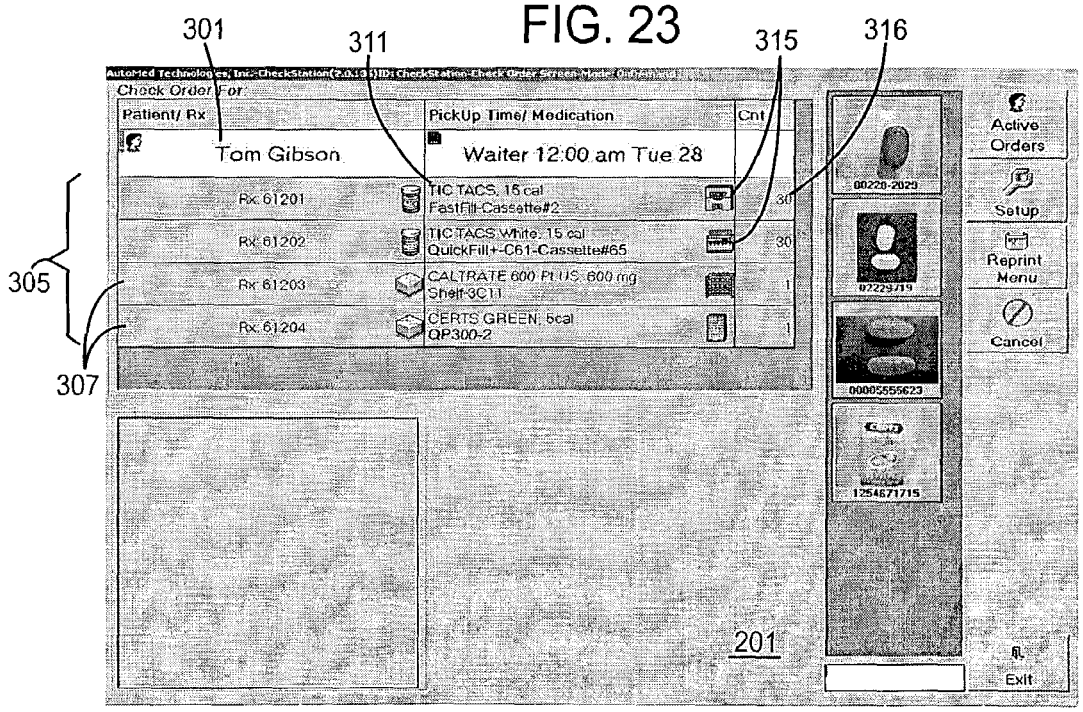
FIG. 23 is a front view of the screen image of FIG. 22 subsequent to initiation of validation by the pharmacist.
Figure 24:
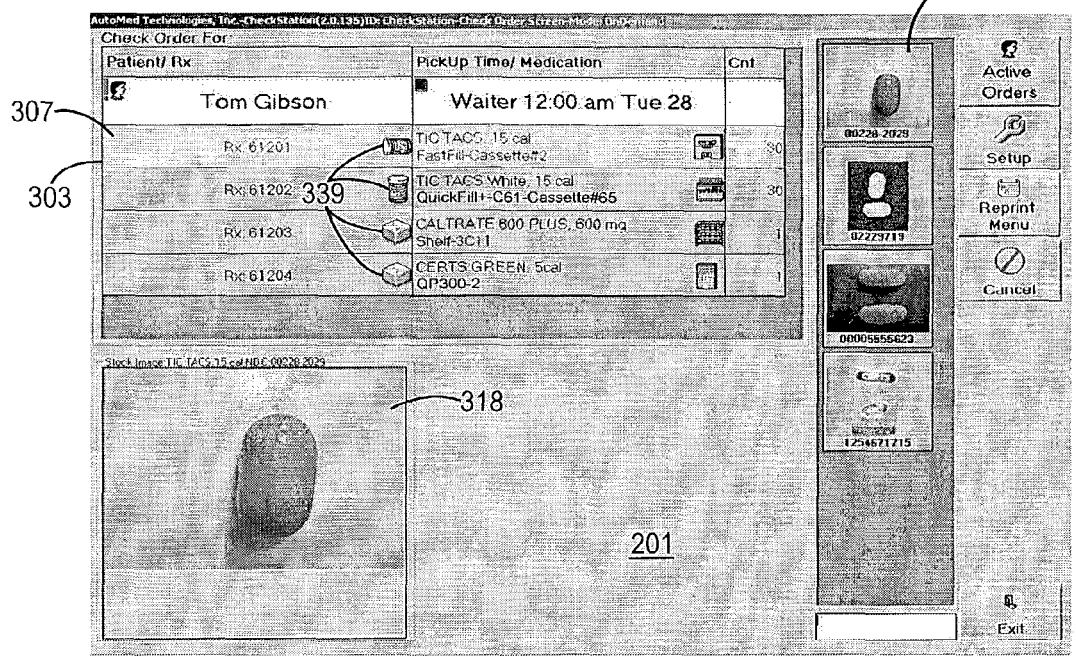
FIG. 24 is a front view of the screen image of FIG. 23 but after selection of the first prescription for validation. An enlarged stock image of the associated medication is provided.
Figure 25:
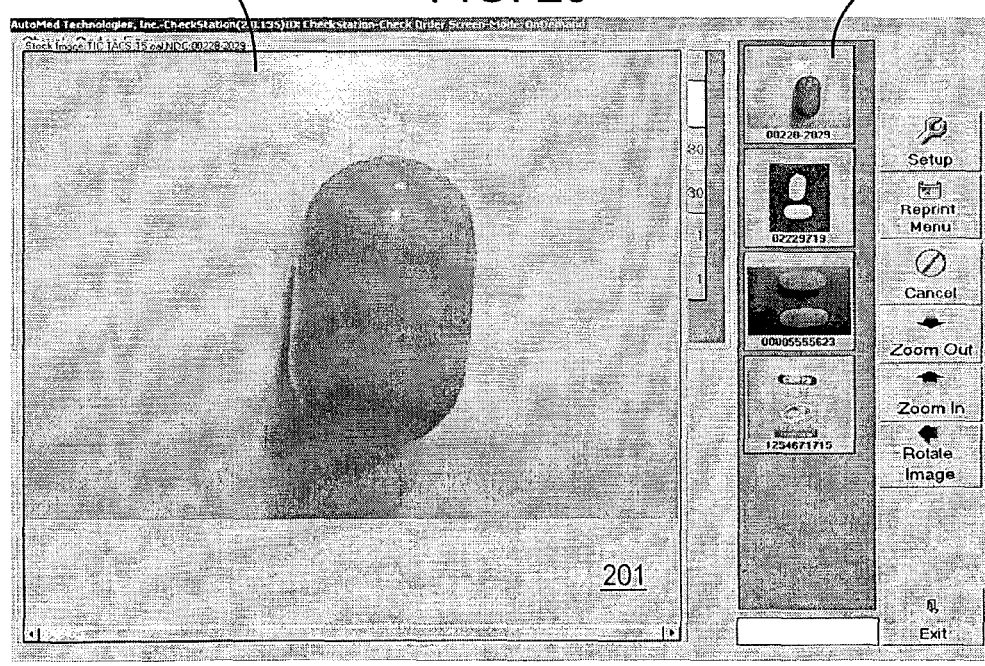
FIG. 25 is a front view of the screen image of FIG. 24 but showing further enlargement of the stock image of the medication.
Figure 26:
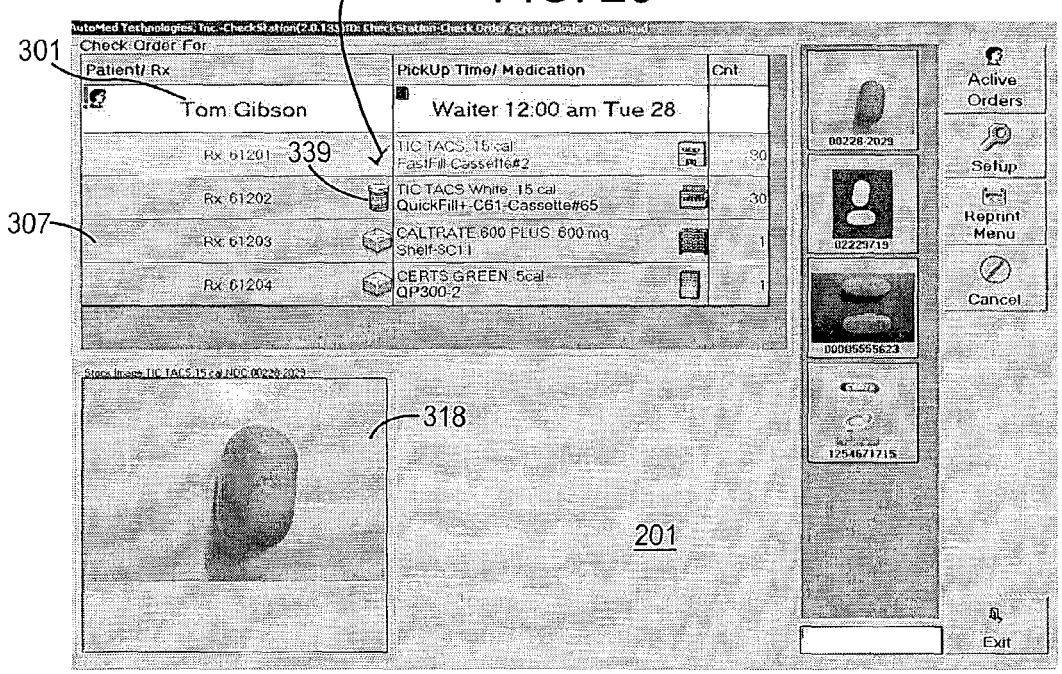
FIG. 26 is a front view of the screen image of FIG. 24 but following validation of the first prescription.

In step 549, the fulfilled prescription order is provided to the pharmacist 241 for validation at validation point 81. Pharmacist 241 selects the prescription order 305 to be validated from the queue of pending prescription orders presented on display 195 by WMS 1 as shown in FIG. 22. In the example, pharmacist 241 selects Mr. Gibson's prescription order 305 for validation by touching the row 303 associated with Mr. Gibson's name. Mr. Gibson's order may be located by scrolling up or down using touch arrows 321 or by searching for the customer name as described above. As shown in FIG. 23, WMS 1 then displays Mr. Gibson's prescription order for validation, removing all other pending prescription orders from view on display 195.

As can be seen on FIG. 23, Mr. Gibson's prescription order includes the four prescriptions 307 in the optimized prescription sequence for that prescription order 305. Each prescription 307 includes the same information as shown in FIG. 10 including the prescription number 309, description of the medication type 311, identification of the medication storage location by address 313 and icon 315 and the medication count 316 for each prescription 307. A stock image 318 of each medication is provided.

Figure 28:
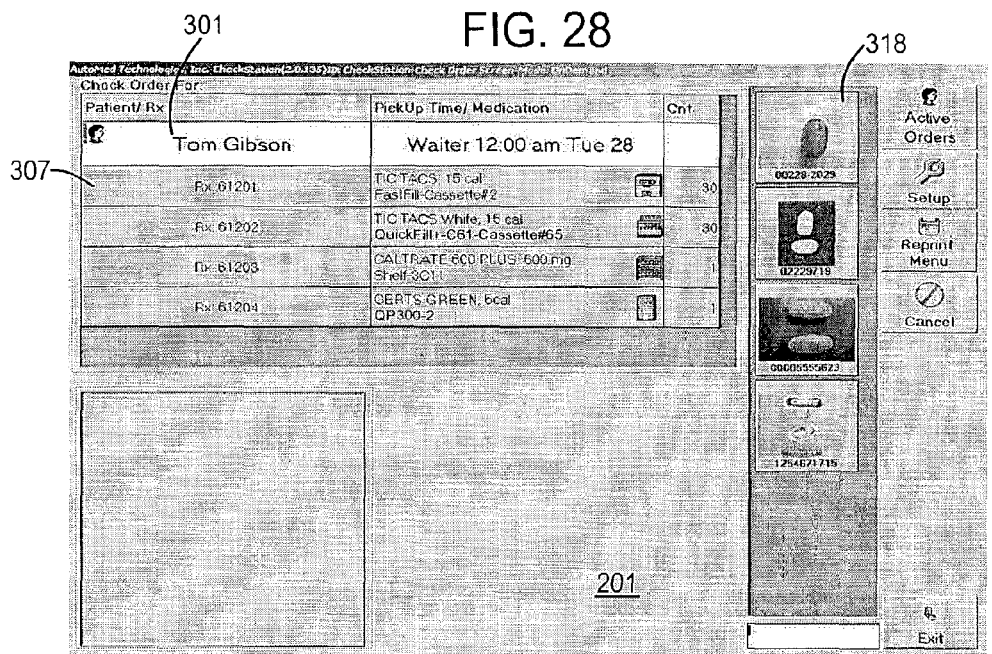
FIG. 28 is a front view of a screen display showing the four filled prescriptions comprising the prescription order in the state where prior verification has not been undertaken. Reference images of the four medications comprising the prescription order are provided.
Figure 29:
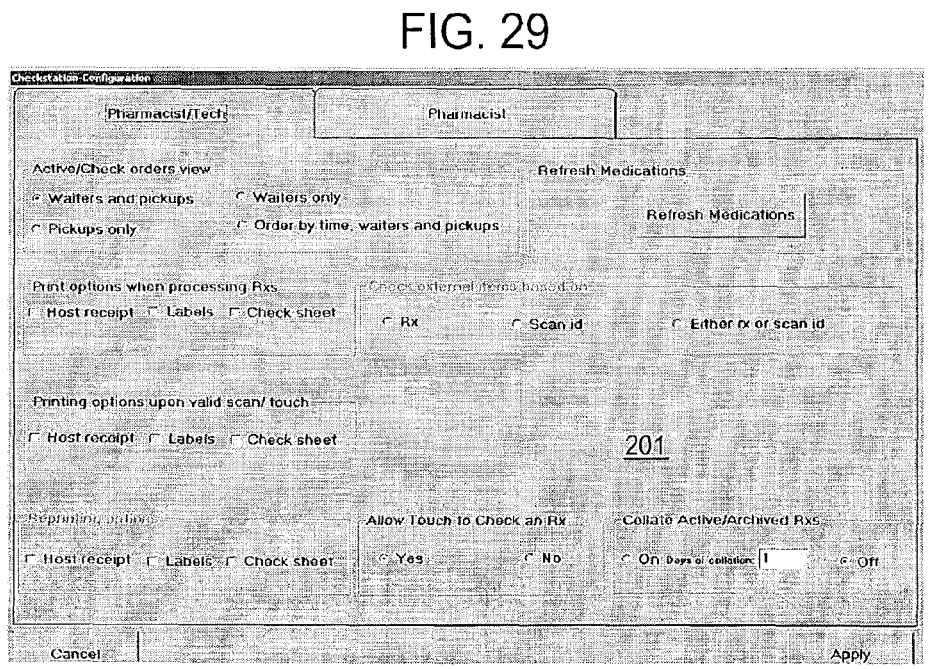
FIG. 29 is a front view of a screen display showing system set up commands.

The package icons 339 associated with each prescription indicate that each prescription has been properly dispensed by the automated dispensers and that manually-selected prescriptions have been duly scan verified by a pharmacist 241 or filling technician 247 to generate the medication_dispensed signal. FIG. 28 represents the state of the order if the prescriptions are not verified as being correctly dispensed. The absence of the package icon 339 for each prescription indicates that heightened scrutiny of the prescription order is warranted.

In step 551, the pharmacist validates the first prescription in the prescription order. The pharmacist 241 selects the prescription to be validated by (1) touching row 303 associated with the prescription 307, (2) by scanning the bar code 278 on label 279 with a scanner 197 or (3) by scanning the prescription bar code 271 on the sequence sheet 269 with reader 197. Selection of the prescription generates a first validation signal received by control computer 209 or another computer in LAN 65.

Pharmacist 241 then visually inspects the dispensed medication and compares the medication to the stock image 318 presented by WMS 1 on display 195. In the case of medications dispensed by a fully automated dispenser 159, the pharmacist 241 would compare the digital image of the medication captured by the dispenser 159 to the stock image 318. As shown in FIGS. 24-27, the stock image 318 can be enlarged by touching the touch screen 201 on stock image 318. The enlarged image 318 assists the pharmacist 241 with the inspection and may be presented together with the customer name, NDC number and medication description. If the prescription has been filled properly, the pharmacist 241 scans the bar code 278 on the label 279 with scanner 197 generating a second validation signal received by control computer 209 or another computer in LAN 65. If the control computer 209 (or other LAN 65 computer) determines that the first and second validation signals are in agreement then the validated prescription is available for release to the customer.

According to step 553, the validation process is repeated for each prescription in the prescription order. The entire prescription order is released once the control computer 209, or other LAN 65 computer, has received agreement on the validation signals for each prescription in the prescription order. The check marks 347 next to each prescription 307 signify that the prescription has been validated.

Validation is completed according to step 555 when the pharmacist 241 places all prescriptions in a bag or other container (not shown) at the pick up point 83 for pick up by the customer 263. Sequence sheet 269 may be used for this purpose.

An optional control may be imposed on validation by requiring entry of a personal identification code indicating authority to validate the prescription order. The identification code may be typed into a data entry field or may be a code on a pharmacist's identification badge which is read by scanner 197 before commencement of validation. WMS 1 denies access to validation for unauthorized pharmacy personnel.

A replenishment process may be provided in the context of the pharmacy with optimized workflow and such replenishment process is embodied by steps 557-563. According to step 557, program 260 updates the quantities in inventory as medications and other articles are dispensed from medication storage locations. Also in step 557, WMS 1 automatically contacts the vendor of the medication or article which has reached a predetermined level of inventory depletion. WMS 1 places an order for replenishment of the inventory with the vendor.

In step 559, the replenishment order is received, processed and fulfilled by the vendor. As part of this step, the vendor sends the ordered medication or article to the pharmacy. Preferably, the medication or product is in a container (not shown) with a machine-readable code (e.g., a bar code) corresponding to the product, including product identification and lot number, a product quantity and an expiration date.

Figure 31:
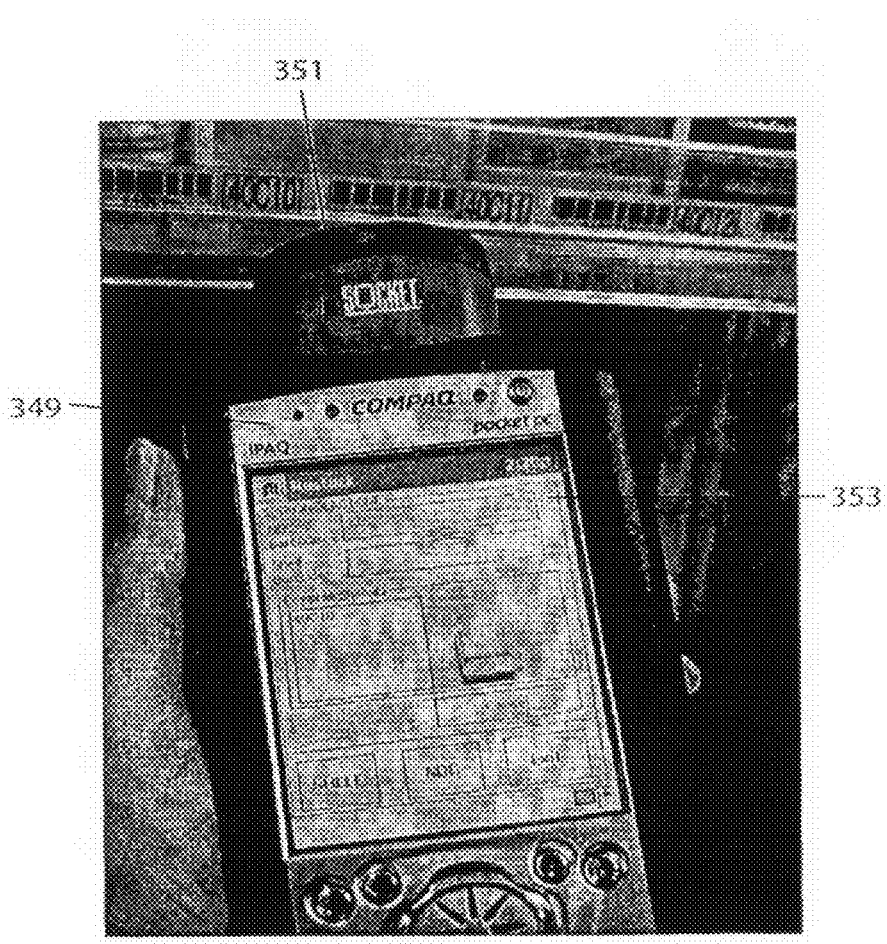
FIG. 31 is a hand held computer useful for practicing a replenishment method according to the invention.

In step 561, a filling technician 247 scans the code on the product received from the vendor and is directed to the appropriate medication storage location in WMS 1. Filling technician 247 may use a hand held computer 349 shown in FIG. 31 for this purpose. Hand held computer 349 includes a machine-readable code scanner 351 and interfaces with LAN 65 and program 260. (The filling technician 241 may optionally initiate replenishment by entering his personal identification code into computer 349 thereby enabling the WMS 1 to identify the person responsible for the replenishment.) Scanned information is entered into computer 349 and information from a database on the computer 349 is presented on the computer display screen 353 providing information directing the filling technician 247 to the medication storage location at which the medication or product is to be stored. The storage location may, for example, be a cassette 101 in dispenser 91, a storage shelf 163 or a location in an automated prepackaged-form medication dispenser 151.

According to step 563, the filling technician 247 then scans a machine-readable code (e.g., code 122, 124, 184) at the designated medication storage location (e.g., cell 173, or shelf 115 in FIG. 3D) and on the product container, preferably using hand held computer 349. If there is agreement between the identified medication and the scanned storage location, the filling technician receives a prompt from computer 349 directing him to replenish the medication.

The filling technician 247 then places the medication or product into the designated storage location completing the replenishment process. The filling technician 247 could also manually enter information about the restocked medication into computer 349. Such manually-entered information could include the product identification and lot number, the precise product quantity placed into inventory and the expiration date.

The information collected on computer 349 is then supplied from computer 349 to program 260 to increment the inventory into the WMS 1 and to provide current medication inventory information to WMS 1, including the exact storage location where the medication is stored and the quantity of medication at that location. The availability of accurate and current medication inventory information to WMS 1 greatly facilitates accurate sequencing of the prescriptions during the prescription order fulfillment process described above. The replenishment process imposes levels of security and control ensuring that the medication inventory database 513 and the actual medication inventory are in complete agreement.

The replenishment process described herein permits the pharmacy operator to not only replenish the inventory but to closely monitor the condition of the medication inventory. For example, the same medication may be stored at different medication storage locations within WMS 1. Such medications may have different expiration dates. By tracking the expiration dates of medication in the medication inventory and by selectively replenishing the older inventory it is possible to maintain a medication inventory including the most potent medications thereby improving service to the customer.

Example and Data

In order to verify the advantages of the present invention, a simulation of pharmacy workflow was performed using a computer model of a typical partially-automated pharmacy layout, the number and type of prescription orders for a typical week, and a normal complement of pharmacy personnel.

The system simulated consisted of an AutoMed FastFill system, an AutoMed QuickFill Plus system, and several static storage shelves.

Comparison was made between this system with no workflow optimization and the same system with the inventive optimization process used to select the storage locations from which to obtain medications and to determine the best sequence in which to fill the prescriptions within each prescription order. The cost function chosen for the simulation was total time to fill prescription orders.

A one-week prescription load of 2205 prescriptions was simulated, including 309 multi-prescription orders with an average of 2.5 prescriptions per multi-prescription order. The improvement achieved in the simulation indicated that under these workload assumptions, there was a 5.5% decrease in the average time required to fill an order.

Of the 309 multi-prescription orders, 219 consisted of two prescriptions and 60 contained three prescriptions. In an order environment in which a higher percentage of the orders are multi-prescription orders having a higher average number of prescriptions per multi-prescription order, an even higher benefit is expected. Further benefit is possible with a cost function which takes into account "neighboring" orders since such a cost function is designed to provide efficiency improvements for some percentage of the single-prescription orders, depending on how many of the medications in the inventory have more than one storage location from which they can be obtained.

* * *

While the principles of the invention have been shown and described in connection with specific embodiments and steps, it is to be understood that such embodiments are by way of example and are not limiting.

What is claimed is:

1. A computerized method for filling a prescription order, comprising:
   receiving by a control computer a prescription order comprising two or more medications, each medication stored at a different location;
   using the control computer to generate a sequence in which to gather the medications of the prescription order at the different locations; and
   generating human-readable indicia of the sequence, the indicia for each medication comprising:
   a name of the medication,
   a stock image of the medication, and
   an icon representative of the location in which the medication is stored;
   wherein the control computer determines the sequence by minimizing a cost function associated with gathering the two or more medications for the fulfillment of the prescription order.

2. The computerized method of claim 1, wherein the human-readable indicia of the sequence is provided on a display.

3. The computerized method of claim 1, wherein the human-readable indicia of the sequence is provided in a printed form.

4. The computerized method of claim 3, wherein the information is printed on a tote bag configured to hold the medications of the prescription order.

5. The computerized method of claim 1, further comprising:
   receiving a digital image of at least one of the medications stored in a dispensing apparatus provided at one of the different locations, the digital image taken by a feature of the dispensing apparatus.

6. The computerized method of claim 5, further comprising:
   displaying the digital image proximate to a display of a stock image of the medication for comparison thereof.

7. The computerized method of claim 1, wherein the cost function includes at least one variable related to the distance required to be traveled between the different locations to fulfill the prescription order.

8. The computerized method of claim 1, wherein the cost function includes variables related to the locations of medications assigned to other prescription orders that are co-pending with the prescription order.

9. A computerized method for filling a prescription order, comprising:
   receiving by a control computer a prescription order comprising two or more medications, each medication stored at a different location;
   using the control computer to generate a sequence in which to retrieve the medications from the different locations, the control computer programmed to generate the sequence based on workflow considerations; and
   generating human-readable indicia of the sequence, wherein the indicia of the sequence is a printed sequence list comprising the following information for each medication:
   a name of the medication,
   a stock image of the medication, and
   an icon representative of the location in which the medication is stored.

10. The computerized method of claim 9, wherein the printed sequence list is printed on a tote bag configured to hold the medications of the prescription order.

11. The computerized method of claim 9, wherein at least one of the workflow considerations includes the distance required to be traveled between the different locations to fulfill the prescription order.

12. The computerized method of claim 9, wherein at least one of the workflow considerations includes the locations of medications assigned to other prescription orders that are co-pending with the prescription order.

13. The computerized method of claim 1, wherein the control computer is programmed to determine the sequence in order to decrease the time needed to fill the prescription order.

14. The computerized method of claim 1, wherein the control computer is programmed to determine the sequence based upon the position of the different locations.

15. A computerized method for filling a prescription order, comprising:
   receiving by a control computer a prescription order, the prescription order including at least one medication to be filled;
   using the control computer to select a storage location at which the at least one medication is stored, the control computer configured to select the storage location based upon reducing the amount of time required to fill the at least one medication from the storage location; and
   generating human-readable indicia of the storage location
   generating human-readable indicia of a name of the at least one medication and a stock image of the at least one medication, wherein the human-readable indicia of the storage location includes an icon representative of the storage location.

16. The computerized method of claim 15, wherein the control computer is configured to select the storage location based upon the travel distance required to fill the at least one medication from the storage location.

17. The computerized method of claim 15, wherein the control computer is configured to select the storage location based upon locations of medications assigned to other prescription orders that are co-pending with the prescription order.

18. The computerized method of claim 15, wherein the human-readable indicia of the storage location is a printed label.

* * * * *